(12) United States Patent
Maruyama et al.

(10) Patent No.: US 6,346,532 B1
(45) Date of Patent: Feb. 12, 2002

(54) AMIDE DERIVATIVES OR SALTS THEREOF

(75) Inventors: Tatsuya Maruyama; Takayuki Suzuki; Kenichi Onda; Masahiko Hayakawa; Hiroyuki Moritomo; Tetsuya Kimizuka; Tetsuo Matsui, all of Tsukuba (JP)

(73) Assignee: Yamanouchi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/529,096

(22) PCT Filed: Oct. 15, 1998

(86) PCT No.: PCT/JP98/04671

§ 371 Date: Apr. 7, 2000

§ 102(e) Date: Apr. 7, 2000

(87) PCT Pub. No.: WO99/20607

PCT Pub. Date: Apr. 29, 1999

(30) Foreign Application Priority Data

Oct. 17, 1997 (JP) .............................. 9-285778

(51) Int. Cl.$^7$ .................... A61K 31/495; A61K 31/505; C07D 239/02; C07D 213/00; C07D 249/00
(52) U.S. Cl. .................... 514/252.1; 514/256; 544/330; 544/332; 546/1; 546/152; 548/190; 548/214; 548/186; 548/252; 548/260
(58) Field of Search ................... 544/330, 332; 546/1, 152; 548/190, 214, 186, 252, 260; 514/252.1, 256

(56) References Cited

U.S. PATENT DOCUMENTS

| | | | | |
|---|---|---|---|---|
| 5,223,614 A | * | 6/1993 | Schromm et al. | 544/105 |
| 5,541,197 A | * | 7/1996 | Fisher et al. | 514/311 |
| 5,553,475 A | | 9/1996 | Hayashi et al. | 72/225 |
| 5,614,544 A | | 3/1997 | Sohda et al. | 514/376 |
| 6,048,884 A | | 4/2000 | Maruyama et al. | 514/370 |
| 6,177,454 B1 | | 1/2001 | Maruyama et al. | 514/394 |

FOREIGN PATENT DOCUMENTS

| | | | |
|---|---|---|---|
| DE | 3743265 | * | 6/1989 |
| JP | 10218861 | * | 6/1989 |
| WO | 9529159 | * | 11/1995 |

OTHER PUBLICATIONS

Konosu T. et al. "Triazole antif.", Chem.Pharm.Bull., 39/10, 2581–9, Oct. 1991.*

* cited by examiner

*Primary Examiner*—Richard L. Raymond
*Assistant Examiner*—Sudhaker B. Patel
(74) *Attorney, Agent, or Firm*—Finnegan, Henderson, Farabow, Garrett & Dunner, L.L.P.

(57) ABSTRACT

(I)

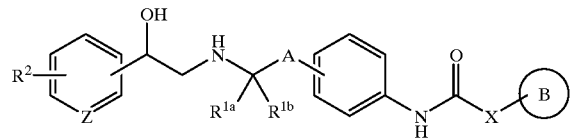

Amide derivatives represented by general formula (I) or salts thereof wherein each symbol has the following meaning: ring B: an optionally substituted heteroaryl optionally fused with a benzene ring; X: a bond, lower alkylene or lower alkenylene optionally substituted by hydroxy or lower alkyl, carbonyl, or a group represented by —NH— (when X is lower alkylene optionally substituted by lower alkyl which may be bonded to the hydrogen atom bonded to a constituent carbon atom of ring B to form lower alkylene to thereby form a ring); A: a lower alkylene or a group represented by -(lower alkylene)—O—; $R^{1a}$ and $R^{1b}$: the same or different and each hydrogen or lower alkyl; $R^2$: hydrogen or halogeno; and Z: nitrogen or a group represented by =CH—. The compounds are useful as a diabetes remedy which not only functions to both accelerate the secretion of insulin and enhance insulin sensitivity but has an antiobestic action and an antihyperlipemic action based on its selective stimulative action on a $\beta_3$ receptor.

14 Claims, No Drawings

AMIDE DERIVATIVES OR SALTS THEREOF

TECHNICAL FIELD

The present invention relates to pharmaceuticals and, more particularly, it relates to novel amide derivatives or salts thereof and also to therapeutic agents for diabetes mellitus containing them as effective components.

BACKGROUND OF THE INVENTION

Diabetes mellitus is a disease accompanied by continuous hyperglycemic state and is said to be resulted by action of many environmental factors and genetic factors. The main controlling factor for blood sugar is insulin, and it has been known that hyperglycemia is resulted by deficiency of insulin or by excess of factors which inhibit its action (such as genetic cause, lack of exercise, obesity and stress).

Diabetes mellitus is classified into two main types. One is insulin-dependent diabetes mellitus (IDDM) caused by a lowering of insulin-secreting function of pancreas due to autoimmune diseases, and another is non-insulin-dependent diabetes mellitus (NIDDM), caused by a lowering of insulin-secreting function of pancrease due to pancreatic fatigue accompanied by continuous high insulin secretion. 95% or more of diabetic patients in Japan are said to suffer from NIDDM, and an increase in the patients due to a change in daily life style is becoming a problem.

As to the therapy of diabetes mellitus, dietetic treatment, therapeutic exercise and remedy of obesity are mainly conducted in mild cases while, when the disease progresses, oral antidiabetic drugs (for example, insulin secretion promoters such as sulfonylurea compounds and insulin sensitivity potentiators which potentiate the sensitivity of insulin) are administered. In severe cases, an insulin preparation is administered. However, there has been a brisk demand for creation of the drugs whereby higher control for blood sugar is possible, and development of antidiabetic drugs having a new mechanism and having high usefulness has been demanded.

U.S. Pat. Nos. 4,396,627 and 4,478,849 describe phenylethanolamine derivatives and disclose that those compounds are useful as drugs for obesity and for hyperglycemia. Action of those compounds is reported to be due to a stimulating action to $\beta_3$-receptors. Incidentally, it has been known that $\beta$-adrenaline receptors are classified into $\beta_1$, $\beta_2$ and $\beta_3$ subtypes, that stimulation of $\beta_1$-receptor causes an increase in heart rate, that stimulation of $\beta_2$-receptor stimulates decomposition of glycogen in muscles, whereby synthesis of glycogen is inhibited, causing an action such as muscular tremor, and that stimulation of $\beta_3$-receptor shows an anti-obesity and an anti-hyperglycemia action (such as decrease in triglyceride, decrease in cholesterol and increase in HDL-cholesterol).

However, those $\beta_3$-agonists also have actions caused by stimulation of $\beta_1$- and $\beta_2$-receptors such as increase in heart rate and muscular tremor, and they have a problem in terms of side effects.

Recently, it was ascertained that $\beta$-receptors have differences to species, and it has been reported that even compounds having been confirmed to have a $\beta_3$-receptor selectivity in rodential animals such as rats show an action due to stimulating action to $\beta_1$- and $\beta_2$-receptors in human being. In view of the above, investigations for compounds having a stimulating action which is selective to $\beta_3$-receptor in human being have been conducted recently using human cells or cells where human receptors are expressed. For example, WO 95/29159 describes substituted sulfonamide derivatives represented by the formula set forth below and discloses that due to their selective stimulating action to $\beta_3$-receptors in human being, they are useful against obesity, hyperglycemia, etc. However, this patent does not specifically disclose an insulin secretion promoting action and an insulin sensitivity potentiating action of those compounds.

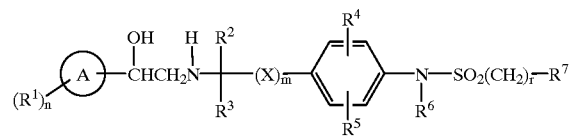

(In the formula, the symbols should be referred to in the specification of this patent.)

As such, there has been still a demand for creation of therapeutic agents for diabetes mellitus of a new type which have a highly clinical usefulness.

DISCLOSURE OF THE INVENTION

The present inventors have conducted an intensive investigation on compounds having both an insulin secretion promoting action and an insulin sensitivity potentiating action and found that novel amide derivatives show both a good insulin secretion promoting action and a good insulin sensitivity potentiating action and furthermore show a selective stimulating action to $\beta_3$-receptors, leading to accomplishment of the present invention.

That is, the present invention relates to an amide derivative represented by the general formula (I) set forth below or a salt thereof that is useful for the therapy of diabetes mellitus, having both an insulin secretion promoting action and an insulin sensitivity potentiating action and further having anti-obesity and anti-hyperlipemia actions due to a selective stimulating action to $\beta_3$-receptors. The present invention also relates to a pharmaceutical agent, particularly to a therapeutic agent for diabetes mellitus containing the amide derivative or the salt thereof as an effective ingredient.

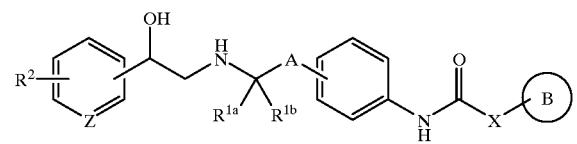

(In the formula, each of the symbols means as follows:
  ring B: a heteroaryl group which may be substituted and may be fused with a benzene ring;
  X: a bond, lower alkylene or alkenylene which may be substituted with hydroxy or a lower alkyl group, carbonyl, or a group represented by —NH— (when X is a lower alkylene group which may be substituted with a lower alkyl group, the hydrogen atoms bonded to the carbon atom constituting the ring B may form a lower alkylene group together with the lower alkyl group so that a ring is formed);
  A: lower alkylene or a group represented by -lower alkylene-O—;
  $R^{1a}$, $R^{1b}$: they may be the same or different and each is a hydrogen atom or a lower alkyl group;
  $R^2$: a hydrogen atom or a halogen atom; and Z: a nitrogen atom or a group represented by =CH—.)

The compound of the general formula (I) is further illustrated as follows.

In the definitions used in the general formula in this specification, the term "lower" means a linear or branched hydrocarbon chain having from 1 to 6 carbon atoms unless otherwise specified.

Specific examples of the "lower alkyl group" are methyl, ethyl, and linear or branched propyl, butyl, pentyl and hexyl, preferably an alkyl having from 1 to 4 carbon atoms, and particularly preferably methyl, ethyl, propyl and isopropyl.

Examples of the "lower alkylene group" is a divalent group obtained by removing an arbitrary hydrogen atom(s) from the above "lower alkyl group", preferably an alkylene group having from 1 to 4 carbon atoms, and particularly preferably methylene, ethylene, propylene and butylene. Examples of the "lower alkenylene group" are vinylene, propenylene, butenylene, pentenylene and hexenylene groups.

The "heteroaryl group which may be fused with a benzene ring" in the "heteroaryl group which may be substituted and may be fused with a benzene ring" means a ring group where a benzene ring is fused with a heteroaryl group as mentioned later or a non-fused heteroaryl group.

Specific examples of the "ring group where the benzene ring is fused with a heteroaryl group" are fused-ring heteroaryl groups such as quinolyl, isoquinolyl, quinazolinyl, quinolidinyl, quinoxalinyl, cinnolinyl, benzimidazolyl, imidazopyridyl, benzofuranyl, benzoisoxazolyl, benzoxazolyl, benzothiazolyl, oxazolopyridyl, isothiazolopyridyl, benzothienyl, etc.; and oxo-added rings such as oxobenzofurayl, etc.

Examples of the "heteroaryl group" are monocyclic heteroaryl groups such as furyl, thienyl, pyrrolyl, imidazolyl, thiazolyl, pyrazolyl, isothiazolyl, isoxazolyl, pyridyl, pyrimidyl, pyridazinyl, pyrazinyl, thiadiazolyl, triazolyl, tetrazolyl, etc.; and bicyclic heteroaryl groups such as naphthylidinyl, pyridopyrimidinyl, etc.

The substituent in the "heteroaryl group which may be substituted and may be fused with a benzene ring" may be any group which can be usually substituted in this ring group. Preferred examples are a halogen atom and lower alkyl, lower alkenyl, lower alkynyl, hydroxy, sulfanyl, halogeno lower alkyl, lower alkyl-O—, lower alkyl-S—, lower alkyl-O—CO—, carboxy, sulfonyl, sulfinyl, lower alkyl-SO—, lower alkyl-SO$_2$—, lower alkyl-CO—, lower alkyl-CO—O—, carbamoyl, lower alkyl-NH—CO—, di-lower alkyl-N—CO—, nitro, cyano, amino, guanidino, lower alkyl-CO—NH—, lower alkyl-SO$_2$—NH—, lower alkyl-NH—, di-lower alkyl-N—, —O-lower alkylene-O—, etc. These substituents may further be substituted with a substituent such as an aryl group, a heteroaryl group, a halogen atom, hydroxy, sulfanyl, halogeno lower alkyl, lower alkyl-O—, lower alkyl-S—, lower alkyl-O—CO—, carboxy, sulfonyl, sulfinyl, lower alkyl-SO—, lower alkyl-SO$_2$—, lower alkyl-CO—, lower alkyl-CO—O—, carbamoyl, lower alkyl-NH—CO—, di-lower alkyl-N—CO—, nitro, cyano, amino, guanidino, lower alkyl-CO—NH—, lower alkyl-SO$_2$—NH—, lower alkyl-NH—, di-lower alkyl-N—, etc. These substituents such as an aryl group, a heteroaryl group, etc. may further be substituted with a halogen atom, etc.

The "lower alkenyl group" is a linear or branched alkenyl group having 2 to 6 carbon atoms, and its specific examples are vinyl, propenyl, butenyl, pentenyl and hexenyl groups.

The "lower alkynyl group" is a linear or branched alkynyl group having 2 to 6 carbon atoms, and its specific examples are ethynyl, propynyl, butynyl, pentynyl and hexynyl.

The "halogen atom" means a fluorine atom, a chlorine atom, a bromine atom or an iodine atom, and the "halogeno lower alkyl group" means a group where an arbitrary hydrogen atom or atoms in the above-mentioned alkyl group is/are substituted with a halogen atom or atoms.

The case when X is a bond means that a carbon atom of the —CO— group is directly bonded to the ring B.

The compound (I) of the present invention has at least one asymmetric carbon atom and therefore, there are optical isomers such as (R)-compounds, (S)-compounds, etc., racemates, diastereomers, etc. The present invention includes all and each of isolated isomers and mixtures thereof. The present invention also includes hydrates, solvates (such as those with ethanol) and polymorphic substances of the compound (I).

The compound (I) of the present invention may form a salt with an acid. Examples of the salt are acid addition salts with mineral acids such as hydrochloric acid, hydrobromic acid, hydroiodic acid, sulfuric acid, nitric acid, phosphoric acid, etc.; and those with organic acids such as formic acid, acetic acid, propionic acid, oxalic acid, malonic acid, succinic acid, fumaric aid, maleic acid, lactic acid, malic acid, citric acid, tartaric acid, carbonic acid, picric acid, methanesulfonic acid, ethanesulfonic acid, glutamic acid, etc.

Manufacturing Method

The compound of the present invention or the salt thereof may be manufactured by application of various synthetic methods utilizing the characteristics of its fundamental skeleton or type of the substituent. Representative manufacturing methods are illustrated as hereunder.

First Manufacturing Method

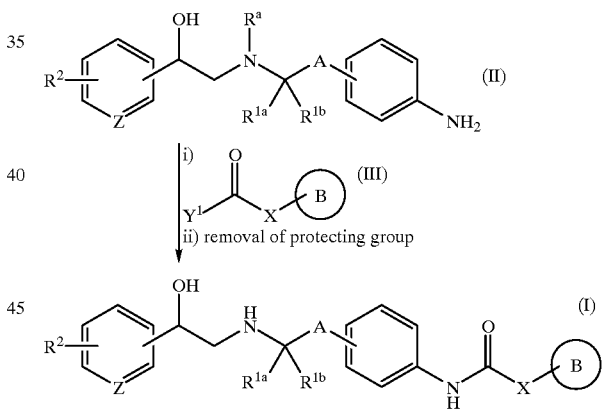

(In the formulae, $R^{1a}$, $R^{1b}$, $R^2$, A, B, X and Z have the same meanings as defined already; $R^a$ is a protective group for amino; and $Y^1$ is a leaving group, and more specifically hydroxy, lower alkoxy or halide.)

In this method, the compound (II) and the compound (III) are subjected to amidation, and the protective group is then removed therefrom to synthesize the compound (I) of the present invention.

The amidation in this manufacturing method can be conducted by customary manners.

The solvent may vary depending upon $Y^1$ of the compound (III) and mostly, an inert solvent or an alcoholic solvent (such as isopropanol, etc.) may be applied.

When $Y^1$ is a hydroxy group, a method where the reaction is conducted in the above-mentioned solvent in the presence of a condensing agent may be applied. Examples of the condensing agent are N,N'-dicyclohexylcarbodiimide (DCC), 1-ethyl-3-(3-dimethylaminopropyl)carbodiimide (EDCI), 1,1'-carbonyldiimidazole (CDI), diphenylphosphoryl azide (DPPA), diethylphosphoryl cyanide (DEPC), etc.

When $Y^1$ is lower alkoxy, a method where the reaction is conducted under heating or refluxing as it is or in the above-mentioned inert solvent may be applied.

When $Y^1$ is halide, a method where the reaction is conducted in the above-mentioned inert solvent in the presence of a base may be applied.

Examples of the inert solvent are dimethylformamide (DMF), dimethylacetamide, tetrachloroethane, dichloromethane, dichloroethane, chloroform, carbon tetrachloride, tetrahydrofuran, dioxane, dimethoxyethane, ethyl acetate, benzene, toluene, xylene, acetonitrile, dimethyl sulfoxide, etc., and mixed solvents thereof, and they may be appropriately selected depending upon each reaction condition. Examples of the base are inorganic bases such as sodium hydroxide, potassium hydroxide, sodium carbonate, potassium carbonate, etc.; and organic bases such as N-methylmorpholine, triethylamine, diisopropylethylamine, pyridine, etc.

The protective group of the amino represented by $R^a$ means a protective group which is commonly used for amino by those skilled in the art, and its representative examples are acyl such as formyl, acetyl, propionyl, methoxyacetyl, methoxypropionyl, benzoyl, thienylacetyl, thiazolylacetyl, tetrazolylacetyl, thiazolylglyoxyloyl, thienylglyoxyloyl, etc.; lower alkoxycarbonyl such as methoxycarbonyl, ethoxycarbonyl, tert-butoxycarbonyl, etc.; aralkyloxy-carbonyl such as benzyloxycarbonyl, p-nitrobenzyloxycarbonyl, etc.; lower alkanesulfonyl such as methanesulfonyl, ethanesulfonyl, etc.; aralkyl such as benzyl, p-nitrobenzyl, benzhydryl, trityl, etc.; tri-(lower alkyl)silyl such as trimethylsilyl, etc.; and the like.

Removal of the protective group in this manufacturing method may be conducted by customary manners. For example, the protective group for amino represented by $R^a$ may be easily removed, for example, by i) a method where in case that the protective group is benzhydryl, p-methoxybenzyl, trityl, tert-butoxycarbonyl, formyl, etc., treatment with an acid such as formic acid, trifluoroacetic acid, a trifluoroacetic acid-anisole mixed solution, a hydrobromic acid-acetic acid mixed solution, a hydrochloric acid-dioxane mixed solution, etc. is conducted; ii) a method where in case that the protective group is benzyl, p-nitrobenzyl, benzhydryl, trityl, etc., a catalytic reduction method using palladium-carbon or palladium hydroxide-carbon is conducted; and iii) a method where in case that the protective group is a tri-(lower alkyl) silyl or the like, treatment with water, fluoride anion (e.g., tetra-n-butylammonium fluoride, sodium fluoride, potassium fluoride, hydrofluoric acid), etc. is conducted.

Second Manufacturing Method

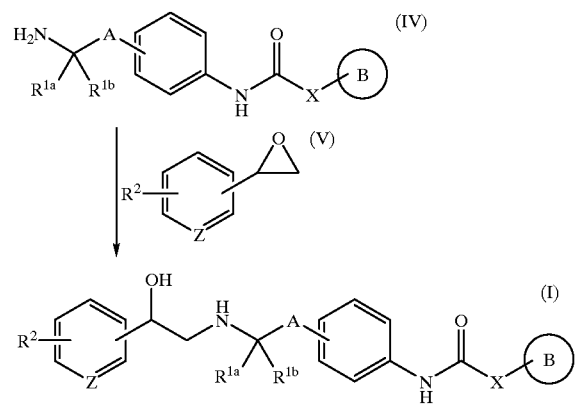

(In the formulae, $R^{1a}$, $R^{1b}$, $R^2$, A, B, X and Z have the same meanings as defined already.)

In this manufacturing method, the compound (IV) is reacted with the compound (V) to give the compound (I) of the present invention.

The amine compound (IV) and the compound (V) are reacted under heating or refluxing for 1 to 24 hours as they are or in an inert solvent, to give the compound (I) of the present invention.

Examples of the inert solvent are acetonitrile, tetrahydrofuran, 2-butanone, dimethyl sulfoxide and N-methylpyrrolidone. In the reaction, a base such as sodium bicarbonate, potassium carbonate or diisopropylethylamine may be added to the reaction mixture.

Incidentally, in the above manufacturing methods, it is possible to purify the resulting substance by removing undesired by-products by means of recrystallization, pulverization, preparative thin layer chromatography, silica gel flash chromatography (as described in W. C. Still, et al., *J. Org. Chem.*, 43, 2923 (1978)), medium-pressure liquid chromatography and HPLC. The compound produced through HPLC can be isolated as a corresponding salt.

The starting material used in the above-mentioned manufacturing methods may be easily manufactured by the methods which are known to those skilled in the art. One of the representative methods is shown as hereunder.

Manufacturing Method for the
Starting Compound (II)

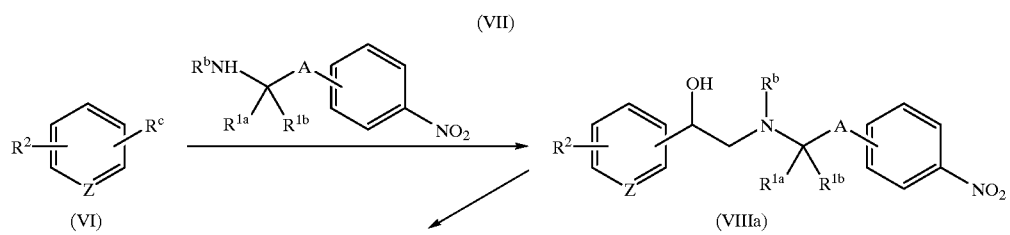

-continued

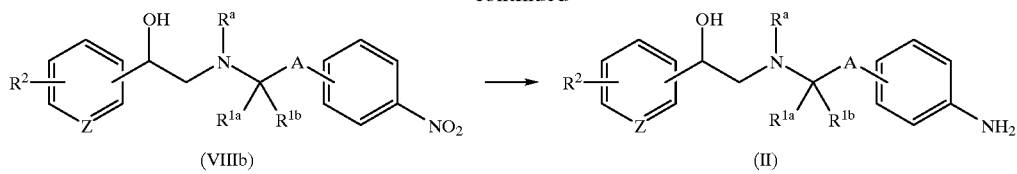

(In the formulae, $R^{1a}$, $R^{1b}$, $R^2$, $R^a$, A and Z have the same meanings as defined already; $R^b$ is a hydrogen atom or an aralkyl-based protective group for amino; and $R^c$ is epoxy, 2-haloacetyl or 1-carboxymethan-1-ol.)

This manufacturing method is composed of from step (a) to step (c) in which the step (a) is a step where the compound (VI) is reacted with the compound (VII), followed by reduction reaction to give the compound (VIIIa) depending upon the type of $R^c$,; the step (b) is a step where protection is conducted when $R^b$ of the compound (VIIIa) is a hydrogen atom; and the step (c) is a step where nitro is reduced to amino to give the compound (II).

Examples of the aralkyl-based protective group for amino used in this manufacturing method are benzyl, p-nitrobenzyl, benzhydryl, etc.

Step (a)

Illustration is made for the following three cases.

1) When $R^c$ is epoxy, the compound (VI) may be reacted with the compound (VII) by the same manner as in the above-mentioned second manufacturing method. Reaction conditions such as reaction temperature, solvent, etc. are the same as well.

2) When $R^c$ is 2-haloacetyl, the compound (VI) is reacted with the compound (VII) in the presence of a base, followed by reduction reaction to prepare the compound (VIIIa). The base is the same as that mentioned in the first manufacturing method. The reduction reaction may be conducted in the above-mentioned inert solvent or in a solvent of an alcohol type with stirring in the presence of a reducing agent. Examples of the reducing agent are sodium borohydride, sodium cyanoborohydride, lithium aluminum hydride, borane, etc.

3) When $R^c$ is 1-carboxymethan-1-ol, the compound (VI) is reacted with the compound (VII) in the presence of a condensing agent, followed by reduction reaction in the same manner as in 2) to prepare the compound (VIIIa). The condensing agent is the same as that mentioned in the first manufacturing method.

Step (b):

When $R^b$ in the compound (VIIIa) is a hydrogen atom, the amino group is protected by customary manners using di-tert-butyl dicarbonate, etc., to prepare the compound (VIIIa).

Step (c):

A method for the reduction of nitro to amino may be conducted by customary manners such as metallic reduction using iron, zinc, etc. and catalytic reduction using a catalyst such as palladium-carbon, palladium hydroxide-carbon, Raney nickel, etc. $R^a$ becomes a hydrogen atom depending upon the reduction conditions, but it may be protected again by customary manners.

Manufacturing Method for Starting Compound (IV)

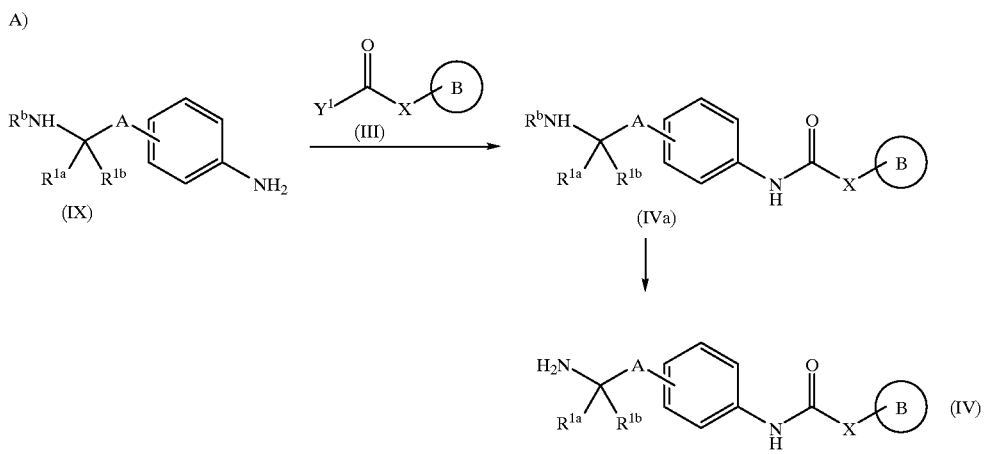

(In the formulae, $R^{1a}$, $R^{1b}$, $R^b$, A, B, X and $Y^1$ have the same meanings as defined already.)

This reaction is a reaction where the compound (IX) and the compound (III) are subjected to amidation reaction to give a compound (IVa) and, when $R^b$ is a protective group for amino, the protective group is removed to give a compound (IV). The amidation reaction can be conducted by the same manner as in the above-mentioned first manufacturing method, and the reaction conditions such as reaction temperature, solvent, etc. are the same as well.

B)

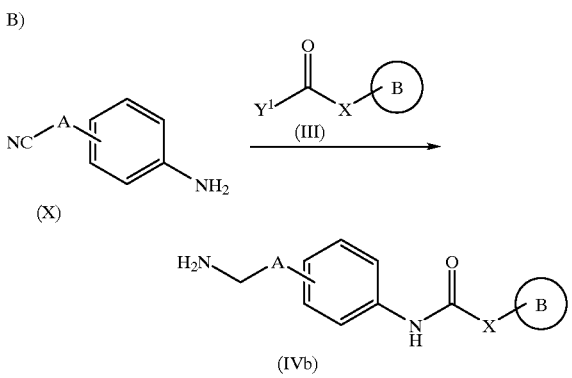

This reaction is a reaction where the compound (X) and the compound (III) are subjected to amidation reaction and then to reduction reaction to give a compound (IVb). The amidation reaction can be conducted by the same manner as in the above-mentioned first manufacturing method, and the reaction conditions such as reaction temperature, solvent, etc. are the same as well. In the reduction reaction, the above-mentioned catalytic reduction, or a method where reduction is conducted using sodium borohydride in the presence of cobalt chloride, may be applied.

With regard to other compounds such as the compound (III), the compound (V), the compound (VI), and the compound (VII), those which are available in the market or are appropriately synthesized by known methods (such as N-alkylation reaction, cyclization reaction, hydrolysis reaction, etc.) from the commercially available compounds may be used.

The compound (I) of the present invention which is manufactured as such is isolated and purified as a free compound, a salt thereof obtained by means of salt formation by customary manners, a hydrate, a solvate with various solvents such as ethanol, etc., or polymorphic crystals, etc. The isolation and purification may be conducted by applying common chemical operations such as extraction, concentration, evaporation, crystallization, filtration, recrystallization, various chromatographic methods, etc.

Various isomers may be isolated by customary manners utilizing the physico-chemical differences between the isomers. For example, the racemate can be converted to stereochemically pure isomers by common racemic resolution (such as a method where the racemate is changed to diastereomer salts with usual optically active acid (for example, tartaric acid), followed by optical resolution, and the like). Incidentally, a mixture of diastereomers may be separated by customary method such as fractional crystallizaiton or chromatography, etc. In the case of an optically active compound, it may be manufactured starting from an appropriate optically active material.

Industrial Applicability

The phenethanol derivative of the present invention represented by the general formula (I) or the salt thereof has both an insulin secretion promoting action and an insulin sensitivity potentiating action and also has a selective $\beta_3$-receptor stimulating action, so that it is useful as a therapeutic agent for diabetes mellitus.

As confirmed by a glucose tolerance test and a hypoglycemic test in insulin-resisting model animals as described later, the compound of the present invention has both a good insulin secretion promoting action and a good insulin sensitivity potentiating action, so that its usefulness in diabetes mellitus is expected. Although the $\beta_3$-receptor stimulating action may have a possibility of participating in expression of the insulin secretion promoting action and the insulin sensitivity potentiating action, other mechanism might also possibly participate therein, and the details thereof have been still unknown yet. The $\beta_3$-receptor stimulating action of the compound of the present invention is selective to $\beta_3$-receptors in human being. It has been known that the stimulation of $\beta_3$-receptor stimulates decomposition of fat (decomposition of the fat tissue triglyceride into glycerol and free fatty acid), whereby a disappearance of fat mass is promoted. Therefore, the compound of the present invention has an anti-obesity action and an anti-hyperlipemia action (such as triglyceride lowering action, cholesterol lowering action and HDL cholesterol increasing action) and is useful as a preventive and therapeutic agent for obesity and hyperlipemia (such as hypertriglyceridemia, hypercholesterolemia and hypo-HDL-lipoproteinemia). Those diseases have been known as animus factors in diabetes mellitus, and amelioration of those diseases is useful for prevention and therapy of diabetes mellitus as well.

The compound of the present invention is also useful as a preventive and therapeutic agent for other diseases where the improvement of symptom can be achieved by reducing the symptoms of obesity and hyperlipemia such as ischemic coronary diseases such as arteriosclerosis, myocardial infarction, angina pectoris, etc. cerebral arteriosclerosis such as cerebral infarction, etc., or aneurysm, etc.

Further, the selective $\beta_3$-receptor stimulating action of the compound of the present invention is useful for prevention and therapy of s several diseases which have been reported to be improved by the stimulation of $\beta_3$-receptor. Examples of those diseases are shown as follows.

It has been mentioned that the $\beta_3$-receptor mediates the motility of non-sphincteral smooth muscle contraction, and because it is believed that the selective $\beta_3$-receptor stimulating action assists the pharmacological control of intestinal motility without being accompanied by cardiovascular action, the compound of the present invention has a possibility of being useful in therapy of the diseases caused by abnormal intestinal motility such as various gastrointestinal diseases including irritable colon syndrome. It is also useful as the therapy for peptic ulcer, esophagitis, gastritis and duodenitis (including that induced by *H. pylori*), enterelcosis (such as inflammatory intestinal diseases, ulcerative colitis, clonal disease and proctitis).

It is further shown that the $\beta_3$-receptor affects the inhibition of release of neuropeptide of some sensory fibers in lung. The sensory nerve plays an important role in neurogenic inflammation of respiratory tract including cough, and therefore, the specific $\beta_3$-agonist of the present invention is useful in the therapy of neurogenic inflammation and in addition, has little action to cariopulmonary system.

Moreover, the $\beta_3$-adrenaline receptor is capable of resulting in a selective antidepressant action due to stimulation of the $\beta_3$-receptor in brain, and accordingly, the compound of the present invention has a possibility of being useful as an antidepressant.

The action of the compound of the present invention has been ascertained to be selective to $\beta_3$-receptors as a result of experiments using cells expressing human type receptors, and the adverse action caused by other $\beta_3$-receptor stimulation is low or none.

Effects of the compound of the present invention have been ascertained by the following tests.

1. Hypoglycemic Test in kk Mice (insulin-resisting model; Obesity and Hyperglycemia)

Male kk mice (blood sugar level: not lower than 200 mg/dl) were subjected to a measurement of blood sugar level under feeding and then randomly classified into groups. The drug to be tested was compulsorily administered orally or subcutaneously once daily for four days, and the blood sugar level after 15 to 18 hours from the final administration was compared with that before the administration (n=6). The blood was collected from a tail vein of the mice using a glass capillary (previously treated with heparin), the protein was removed therefrom, and the amount of glucose in the supernatant liquid (mg/dl) was measured by calorimetric determination by means of a glucose oxidase method. Further, a dose at which the blood sugar level was lowered by 30% as compared with that before the administration with the drug to be tested was expressed as an $ED_{30}$ value.

As a result, the compound of the present invention significantly lowered the blood sugar level as compared with that before the administration with the drug to be tested in both cases of oral and subcutaneous administrations. In particular, some of the compounds of the present invention exhibited a strong activity so that the $ED_{30}$ value in the oral administration was 3 mg/kg/day or less. On the other hand, in the above-referenced WO 95/29159, the compound of Example 90 had an $ED_{30}$ value of 30 mg/kg/day or more, and the compound of Example 92 had an $ED_{30}$ value of 30 mg/kg/day. From this fact, it has become clear that the compounds of the present invention have a superior potentiating action to insulin sensitivity as compared with those of the above-referenced WO 95/29159.

2. Glucose Tolerance Test in Normal Rats

Male rats of SD strain of seven weeks age were fasted for a whole day and night, then randomly classified into groups and subjected to an oral glucose tolerance test (OGTT) (n+4). The compound to be tested was administered orally or subcutaneously at 30 minutes before administration of glucose (2 g/kg by oral administration). The blood was collected from an abdominal aorta using a heparin-treated glass syringe from the rats which were anesthetized with pentobarbital (65 mg/kg), the protein was removed therefrom, and the amount of glucose in the supernatant liquid (mg/dl) was measured by colorimetric determination by means of a glucose oxidase method. The insulin value in blood was determined by measuring the amount of insulin in plasma (ng/ml) by means of radioimmunoassay (RIA).

As a result, in a group where the compound of the present invention was administered orally or subcutaneously, a significant increase in the insulin value in blood was observed as compared with the group to which no drug was given. An increase in the sugar blood level after administration of glucose was significantly inhibited as well. From those results, it is apparent that the compound of the present invention has a good insulin secretion promoting action and a good hyperglycemia inhibiting action.

3. Stimulating Test to Human $\beta_3$-, $\beta_2$- and $\beta_1$-receptors

Human $\beta_3$-stimulating action was investigated using an SK-N-MC cell system (cells in which human $\beta_3$-receptor and human $\beta_1$-receptor were permanently expressed were purchased) while human $\beta_2$- and $\beta_1$-stimulating actions were investigated using a CHO cell system (cells in which each of human $\beta_2$- and $\beta_1$-receptors was compulsorily expressed were purchased). Stimulating action of the compound ($10^{-10}$ to $10^{-4}$ M) were investigated by incubating $10^5$ cells/well of each of the cells on a 24-well plate and checking under a subconfluent state after two days using a producing activity of cyclic AMP (cAMP) as an index. Incidentally, the human $\beta_3$-stimulating action was investigated in the presence of a $\beta_1$-receptor blocker (CGP20712A, $10^{-6}$ M). Amount of production of cAMP in each cell (pmol/ml) was measured by an RIA method using $^{125}$I-cAMP. Intensity of action of each compound was compared by calculating the pD2 value and the maximum activity (I.A. (%) where the maximum reaction of $10^{-6}$ M isoproterenol was defined as 100%) from the resulting dose-reaction curve.

As a result, it has been ascertained that the compound of the present invention has a selective stimulating action to human $\beta_3$-receptor.

A pharmaceutical composition containing one or more of the compound of the present invention or the salt thereof as an effective ingredient is prepared using common pharmaceutically acceptable vehicles. Administration of the pharmaceutical composition according to the present invention may be either by oral administration or by parenteral administration by, for example, injection, suppository, subcutaneous agent, inhaling agent or intracystic infusion.

The dose may be appropriately decided depending upon each particular case while taking into consideration symptom, age, sex, etc. of the patient but usually, is around 0.01 mg/kg to 100 mg/kg per day for adults in the case of oral administration, and that is administered at a time or by dividing into 2 to 4 times a day. When intravenous injection is conducted depending upon the symptom, the dose is usually around 0.001 mg/kg to 10 mg/kg per day for adults, and that is administered at a time or by dividing into two or more times a day.

With regard to a vehicle for the preparation, nontoxic solid or liquid substances for pharmaceuticals may be used.

Examples of the solid composition for use by means of oral administration according to the present invention are tablets, pills, capsules, diluted powder and granules. In such a solid composition, one or more active substances are mixed with at least one inert excipient such as lactose, mannitol, glucose, hydroxypropyl cellulose, microcrystalline cellulose, starch, polyvinylpyrrolidone, agar, pectin, magnesium metasilicate aluminate and magnesium aluminate. The composition may also contain additives other than the inert excipient such as lubricants such as magnesium stearate; disintegrants such as calcium cellulose glycolate; stabilizers such as lactose; and auxiliary solubilizers such as glutamic acid or aspartic acid by customary manners. Tablets and pills may, if necessary, be coated with sugar coat such as sucrose, gelatin, hydroxypropyl cellulose, hydroxypropylmethyl cellulose phthalate, etc., or with film of gastric or enteric coating substances.

The liquid composition for oral administration includes pharmaceutically acceptable emulsions, solutions, suspensions, syrups and elixirs and contains commonly used inert excipients such as purified water or ethanol. In addition to the inert excipient, the composition may further contain auxiliary agents such as moisturizing or suspending agents, sweeteners, tasting agents, aromatic agents and antiseptic agents. The injection for parenteral administration includes aseptic aqueous or non-aqueous solutions, suspensions and emulsions. The non-aqueous solutions and suspensions include, for example, distilled water for injection and a physiological saline solution. Examples of the solvent for non-aqueous solution and suspension are propylene glycol; polyethylene glycol; plant oils such as cacao butter, olive oil and sesame oil; alcohols such as ethanol; gum arabic; and Polysolvate 80 (trade name). Such a composition may further contain auxiliary agents such as isotonizing agents; antiseptic agents; moisturizing agents; emulsifiers; dispersing agents; stabilizers such as lactose; and auxiliary solubilizers such as glutamic acid and aspartic acid). These may be sterilized, for example, by filtration passing through a bacteria-preserving filter or by compounding of or irradiation with a bactericide. These may also be used by manufacturing a sterile solid composition, followed by dissolving in sterile water or a sterile solvent for injection before use.

Best Mode for Carrying Out the Invention

The present invention is further illustrated by way of Examples as hereunder. Compounds of the present invention are not limited to those mentioned in the following Examples but cover all of the compounds represented by the above general formula (I), salts thereof, hydrates thereof, geometric and optical isomers thereof and polymorphic forms thereof. Incidentally, the case where the material which is used in the present invention is novel is illustrated by way of the following Referential Example.

REFERENTIAL EXAMPLE 1

To a mixed solution of ethyl acetate and a 1N aqueous solution of sodium hydroxide was added 25.2 g of 4-nitrophenyl ethylamine hydrochloride, and the mixture was vigorously stirred. The organic layer was dried over anhydrous magnesium sulfate, and the solvent was evaporated. To the resulting residue were added 100 ml of 2-propanol and 15.0 g of (R)-styrene oxide successively, and the reaction mixture was heated to reflux for 12 hours. The solvent was evaporated in vacuo, and the residue was purified by silica gel column chromatography (eluent: chloroform/methanol=100/1→10/1) The resulting residue was again subjected to silica gel column chromatography (eluent: hexane/ethyl acetate/triethylamine=1/5/trace) to give 8.05 g of (R)-1-phenyl-2-[[2-(4-nitrophenyl) ethyl]amino]ethanol.

REFERENTIAL EXAMPLE 2

A solution of 8.02 g of (R)-1-phenyl-2-[[2-(4-nitrophenyl) ethyl]amino]ethanol and 6.30 g of di-tert-butyl dicarbonate in 80 ml of tetrahydrofuran was stirred for 12 hours at room temperature. The residue obtained by evaporation of the solvent was purified by silica gel column chromatography (eluent: hexane/ethyl acetate=3/1) to give 10.8 g of tert-butyl (R)-N-(2-hydroxy-2-phenylethyl)-N-[2-(4-nitro-phenyl) ethyl]carbamate.

REFERENTIAL EXAMPLE 3

To a solution of tert-butyl (R)-N-(2-hydroxy-2-phenylethyl)-N-[2-(4-nitrophenyl)ethyl]carbamate in 200 ml of ethanol was added 1.03 g of 10% palladium-carbon and the mixture was stirred for two hours at room temperature in a hydrogen atmosphere under atmospheric pressure. Insoluble matters were removed using Celite, and the filtrate was concentrated in vacuo to give 9.54 g of tert-butyl (R)-N-[2-(4-aminophenyl)-N-(2-hydroxy-2-phenylethyl) ethyl]-carbamate.

REFERENTIAL EXAMPLE 4

To a solution of 448 mg of tert-butyl (R)-N-[2-(4-aminophenyl)-N-(2-hydroxy-2-phenylethyl)ethyl] carbamate and 330 mg of triethylamine in 4 ml of chloroform was added 146 mg of 2-pyridinecarbonyl chloride. The reaction solution was stirred at room temperature for two hours, and the solvent was evaporated in vacuo. The residue was diluted with chloroform, and the organic layer was washed with a saturated aqueous solution of sodium hydrogen carbonate and dried over anhydrous magnesium sulfate. The residue obtained by evaporating the solvent in vacuo was purified by silica gel column chromatography (eluent: hexane/ethyl acetate=1/3) to give 321 mg of tert-butyl (R)-N-(2-hydroxy-2-phenylethyl)-N-[2-[4-[(2-pyridinecarbonyl)amino]phenyl]ethyl]carbamate.

REFERENTIAL EXAMPLE 5

To a solution of 377 mg of tert-butyl (R)-N-[2-(4-aminophenyl)-N-(2-hydroxy-2-phenylethyl)ethyl] carbamate in 10 ml of tetrahydrofuran were added 203 mg of 1-ethyl-3-(3-dimethylaminopropyl)carbodiimide hydrochloride, 143 mg of 1-hydroxybenzotriazole and 202 mg of 8-quinolinecarboxylic acid successively. The reaction solution was stirred at room temperature for 18.5 hours, and the solvent was evaporated in vacuo. The residue was diluted with ethyl acetate, and the organic layer was washed with a saturated aqueous solution of sodium hydrogen carbonate and dried over anhydrous magnesium sulfate. The residue obtained by evaporation of the solvent was purified by silica gel column chromatography (eluent: hexane/ethyl acetate=2/1) to give 302 mg of tert-butyl (R)-N-(2-hydroxy-2-phenylethyl)-N-[2-[4-[(8-quinolinecarbonyl)amino] phenyl]ethyl]carbamate.

REFERENTIAL EXAMPLE 6

To a solution of 403 mg of tert-butyl (R)-N-(2-hydroxy-2-phenylethyl)-N-[2-[4-[(2-1H-imidazol-2-ylacetyl)amino] phenyl]ethyl]carbamate in 10 ml of acetonitrile were added 120 mg of potassium carbonate and 164 mg of 2-fluorobenzyl bromide successively at room temperature. The reaction solution was stirred at 50° C. for 12 hours. Insoluble matters were filtered off using Celite, and the solvent was evaporated. The resulting residue was purified by silica gel column chromatography to give 253 mg of tert-butyl (R)-N-[2-[4-[[2-[1-(2-fluorobenzyl)-1H-imidazol-2-yl]-acetyl]amino]phenyl]ethyl]-N-(2-hydroxy-2-phenylethyl)-carbamate.

REFERENTIAL EXAMPLE 7

To a solution of 13.4 g of (R)-2-[N-benzyl-N-[2-(4-nitrophenyl)ethyl]amino]-1-phenylethanol in 150 ml of methanol were added 8.6 g of iron powder and 40 ml of a 2N aqueous hydrochloric acid solution. The reaction mixture was heated to reflux for two hours, a 1N aqueous solution of sodium hydroxide was added thereto, and the insoluble matters thus produced were filtered off using Celite. The filtrate was concentrated in vacuo to remove the methanol. The resulting aqueous phase was extracted with chloroform, the organic layer was dried over anhydrous magnesium sulfate, and the solvent was evaporated in vacuo. The resulting residue was purified by silica gel column chromatography (eluent: hexane/ethyl acetate=1/1) to give 11.45 g of (R)-2-[N-[2-(4-amino-phenyl)ethyl]-N-benzylamino]-1-phenylethanol.

REFERENTIAL EXAMPLE 8

To 502 mg of (R)-2-[N-[2-(4-aminophenyl)ethyl]-N-benzylamino]-1-phenylethanol were added 336 mg of ethyl 2-(3-methylpyridin-2-yl)acetate and 10 ml of xylene. The reaction mixture was refluxed for nine hours, and the solvent was evaporated in vacuo. The resulting residue was purified by silica gel column chromatography (eluent: hexane/ethyl acetate=1/3) to give 222 mg of (R)-4'-[2-[N-benzyl-N-(2-hydroxy-2-phenylethyl)amino]ethyl3-2-(3-methylpyridin-2-yl)acetanilide.

REFERENTIAL EXAMPLE 9

To a solution of 0.96 g of 2-fluoroacetophenone in 20 ml of tetrahydrofuran was added 2.65 g of benzyltrimethylammonium tribromide. The reaction mixture was stirred at room temperature for 30 minutes, insoluble matters were filtered off, and the solvent was concentrated in vacuo. The resulting residue was dissolved in 40 ml of 2-butanone, then 1.81 g of N-benzyl-4-nitrophenethylamine and 0.92 g of diisopropyl ethylamine were added, and the reaction mixture was heated to reflux for one hour. The solvent was evaporated in vacuo, ethyl acetate was added thereto, and the mixture was washed with water and a saturated saline solution successively. The organic layer was dried over anhydrous magnesium sulfate and evaporated in vacuo. The resulting residue was dissolved in 40 ml of methanol, 0.34 g of sodium borohydride was added thereto, and the reaction mixture was stirred at room temperature for one hour. The solvent was evaporated in vacuo, ethyl acetate was added, and the mixture was washed with water and a saturated saline solution successively. The organic layer was dried over anhydrous magnesium sulfate and evaporated in vacuo. The resulting residue was purified by silica gel column chromatography (eluent: chloroform) to give 1.95 g of 2-[N-benzyl-N-[2-(4-nitrophenyl)ethyl]amino]-1-(2-fluorophenyl)ethanol.

REFERENTIAL EXAMPLE 10

A reaction mixture of 5.12 g of methyl 2-pyridylacetate, 5.14 g of 4-aminobenzyl cyanide and 50 ml of xylene was heated to reflux for 24 hours. An appropriate amount of the solvent was evaporated, diethyl ether was added to the residue, and the resulting crystals were taken by filtration to give 5.65 g of 4'-cyanomethyl-2-(2-pyridyl)acetanilide.

REFERENTIAL EXAMPLE 11

To a solution of 640 mg of 4'-cyanomethyl-2-(4,6-dimethyl-2-pyridyl)acetanilide in 15 ml of tetrahydrofuran was added 15 ml of an ethanolic suspension of a Raney nickel, and concentrated aqueous ammonia was added to adjust the pH of the mixture to about 10. The mixture was stirred at room temperature for one hour in a hydrogen atmosphere under atmospheric pressure. The reaction mixture was filtered using Celite, and the solvent was evaporated in vacuo to give 640 mg of 4'-(2-aminomethyl)-2-(4, 6-dimethyl-2-pyridyl)acetanilide.

REFERENTIAL EXAMPLE 12

To a solution of 630 mg of 4'-(2-aminomethyl)-2-(4,6-dimethyl-2-pyridyl)acetanilide in 20 ml of toluene was added 0.27 ml of benzaldehyde, and the mixture was heated to reflux for three hours using a Dean-Starke apparatus. The reaction mixture was filtered, and the solvent was evaporated in vacuo. A solution of the resulting residue in 30 ml of methanol was cooled at 0° C., 63 mg of sodium borohydride was added, and the mixture was stirred at 0° C. for one hour. About one-half of the solvent of the reaction mixture was evaporated in vacuo, water and ethyl acetate were added to the residue, the organic layer was washed with a saturated saline solution twice and dried over anhydrous magnesium sulfate and the solvent was evaporated in vacuo. To a solution of the resulting residue in 50 ml of isopropanol was added 0.26 ml of (R)-styrene oxide, and the mixture was heated to reflux for 12 hours. The solvent was evaporated in vacuo, and the resulting residue was purified by silica gel column chromatography (eluent: chloroform/methanol= 100/3) to give 920 mg of (R)-4'-[2-[N-benzyl-N-(2-hydroxy-2-phenylethyl)-amino]ethyl]-2-(4,6-dimethyl-2-pyridyl)acetanilide.

EXAMPLE 1

A 4N hydrogen chloride-ethyl acetate solution (10 ml) was added to 10 ml of an ethanolic solution of 458 mg of tert-butyl (R)-N-(2-hydroxy-2-phenylethyl)-N-[2-[4-[(2-pyridinecarbonyl)amino]phenyl]ethyl]carbamate. The reaction solution was stirred at room temperature for three hours, and the solvent was then evaporated in vacuo. The obtained crude crystals were recrystallized from methanol-ethanol-ethyl acetate to give 289 mg of (R)-4'-[2-[(2-hydroxy-2-phenyl-ethyl)amino]ethyl]-2-pyridinecarboxanilide dihydrochloride.

The compounds of Examples 2 to 33 were prepared by the same manner as in Example 1.

EXAMPLE 2

(R)-4'-[2-[(2-Hydroxy-2-phenylethyl)amino]ethyl]-3-pyridinecarboxanilide dihydrochloride

EXAMPLE 3

(R)-41-[2-[(2-Hydroxy-2-phenylethyl)aminolethyl]-8-quinolinecarboxanilide dihydrochloride

EXAMPLE 4

(R)-4'-[2-[(2-Hydroxy-2-phenylethyl)amino]ethyl]-(E)-3-(2-pyridyl)acrylic anilide dihydrochloride

EXAMPLE 5

(R)-2-(Benzothiazol-2-yl)-4'-[2-[(2-hydroxy-2-phenyl-ethyl)amino]ethyl]acetanilide dihydrochloride

EXAMPLE 6

(R)-4'-[2-[(2-Hydroxy-2-phenylethyl)amino]ethyl]-2-(imidazo[2,1-b]thiazol-3-yl)acetanilide dihydrochloride

EXAMPLE 7

(R)-4'-[2-[(2-Hydroxy-2-phenylethyl)amino]ethyl]-2-(2-methylthiazol-4-yl)acetanilide hydrochloride

EXAMPLE 8

(R)-4'-[2-[(2-Hydroxy-2-phenylethyl)amino]ethyl]-2-(1H-imidazol-2-yl)acetanilide dihydrochloride

EXAMPLE 9

(R)-4'-[2-[(2-Hydroxy-2-phenylethyl)amino]ethyl]-2-(1H-tetrazol-5-yl)acetanilide hydrochloride

EXAMPLE 10

(R)-4'-[2-[(2-Hydroxy-2-phenylethyl)amino]ethyl]-2-(5-sulfanyl-1H-1,2,4-triazol-3-yl)acetanilide hydrochloride

EXAMPLE 11

(R)-2-(2-Aminothiazol-4-yl)-4'-[2-[(2-hydroxy-2-phenyl-ethyl)amino]ethyl]-2-oxoacetanilide dihydrochloride

EXAMPLE 12

(R)-2-(5-Amino-1,2,4-thiadiazol-3-yl)-4'-[2-[(2-hydroxy-2-phenylethyl)amino]ethyl]acetanilide dihydrochloride

EXAMPLE 13

(R)-2-(5-Ethoxycarbonylamino-1,2,4-thiadiazol-3-yl)-4'-[2-[(2-hydroxy-2-phenylethyl)amino]ethyl]acetanilide hydrochloride

EXAMPLE 14

(R)-2-[(2-(3-Fluorophenylamino) thiazol-4-yl)-4'-[2-[(2-hydroxy-2-phenylethyl)amino]ethyl]acetanilide dihydrochloride

EXAMPLE 15

(R)-2-(2-Chloropyridin-6-yl)-4'-[2-[(2-hydroxy-2-phenyl-ethyl)amino]ethyl]acetanilide hydrochloride

EXAMPLE 16

(R)-2-(2-Benzyloxypyridin-6-yl)-4'-(2-[(2-hydroxy-2-phenylethyl)amino]ethyl]acetanilide hydrochloride

EXAMPLE 17

(R)-4'-[2-[(2-Hydroxy-2-phenylethyl)amino]ethyl]-2-[1-(2-methyl-3-propenyl)-1H-imidazol-2-yl)acetanilide dihydrochloride

EXAMPLE 18

(R)-2-(1-Benzyl-1H-imidazol-4-yl)-4'-[2-[(2-hydroxy-2-phenylethyl)amino]ethyl]acetanilide dihydrochloride

EXAMPLE 19

(R)-2-[1-(2-Chlorobenzyl)-1H-imidazol-4-yl]-4'-[2-[(2-hydroxy-2-phenylethyl)amino]ethyl]acetanilide dihydrochloride

EXAMPLE 20

(R)-2-[1-(3-Chlorobenzyl)-1H-imidazol-4-yl]-4'-[2-[(2-hydroxy-2-phenylethyl)amino]ethyl]acetanilide dihydrochloride

EXAMPLE 21

(R)-2-[1-(4-Chlorobenzyl)-1H-imidazol-4-yl]-4'-[2-[(2-hydroxy-2-phenylethyl)amino]ethyl]acetanilide dihydro-chloride

EXAMPLE 22

(R)-2-[1-(4-Fluorobenzyl)-1H-imidazol-2-yl]-4'-[2-[(2-hydroxy-2-phenylethyl)amino]ethyl]acetanilide dihydrochloride

EXAMPLE 23

(R)-2-[1-(4-Chlorobenzyl)-1H-imidazol-2-yl]-4'-[2-[(2-hydroxy-2-phenylethyl)amino]ethyl]acetanilide dihydrochloride

EXAMPLE 24

(R)-2-[1-(4-Bromobenzyl)-1H-imidazol-2-yl]-4'-[2-[(2-hydroxy-2-phenylethyl)amino]ethyl]acetanilide dihydrochloride

EXAMPLE 25

(R)-4'-[2-[(2-Hydroxy-2-phenylethyl)amino]ethyl]-2-[1-(4-iodobenzyl)-1H-imidazol-2-yl]acetanilide dihydrochloride

EXAMPLE 26

(R)-4'-[2-[(2-Hydroxy-2-phenylethyl)amino]ethyl]-2-[1-(4-trifluoromethylbenzyl)-1H-imidazol-2-yl]acetanilide dihydrochloride

EXAMPLE 27

(R)-4'-[2-[(2-Hydroxy-2-phenylethyl)amino]ethyl]-2-[1-(2-naphthyl)-1H-imidazol-2-yl]acetanilide dihydrochloride

EXAMPLE 28

(R)-2-[1-(4-Fluorobenzyl)-5-methyl-1H-imidazol-2-yl]-4'-[2-[(2-hydroxy-2-phenylethyl)amino]ethyl]acetanilide dihydrochloride

EXAMPLE 29

(R)-2-[1-(4-Fluorobenzyl)-4-methyl-1H-imidazol-2-yl]-4'-[2-[(2-hydroxy-2-phenylethyl)amino]ethyl]acetanilide dihydrochloride

EXAMPLE 30

(R)-2-[1-(4-Fluorobenzyl)-1H-tetrazol-5-yl]-4'-[2-[(2-hydroxy-2-phenylethyl)amino]ethyl]acetanilide hydrochloride

EXAMPLE 31

(R)-2-[2-(3,4-Dichlorobenzyl)-1H-tetrazol-5-yl]-4'-[2-[(2-hydroxy-2-phenylethyl)amino]ethyl]acetanilide hydrochloride

EXAMPLE 32

(R)-2-[2-(4-Fluorobenzyl)-1H-tetrazol-5-yl]-4'-[2-[(2-hydroxy-2-phenylethyl)amino]ethyl]acetanilide hydrochloride

EXAMPLE 33

(R)-2-[1-(3,4-Dichlorobenzyl)-1H-tetrazol-5-yl]-4'-[2-[(2-hydroxy-2-phenylethyl)amino]ethyl]acetanilide hydrochloride

EXAMPLE 34

To a solution of 175 mg of tert-butyl (R)-N-[2-[4-[2-(1H-1,2,4-triazol-3-yl)acetylaminolphenyl]ethyl]N-(2-hydroxy-2-phenylethyl) carbamate in 5 ml of methanol was added 4 ml of a solution of 4N hydrogen chloride in ethyl acetate. The mixture was stirred at room temperature for three hours, the solvent was filtered off, and the resulting powder was washed with ethanol. The resulting powder was dried to give 125 mg of (R)-4'-[2-[(2-hydroxy-2-phenylethyl)amino]ethyl]-2-(1H-1,2,4-triazol-3-yl)acetanilide dihydrochloride.

The compounds of Examples 35 to 40 were prepared by the same manner as in Example 34.

EXAMPLE 35

(R)-2-(5-Benzylsulfanyl-1H-1,2,4-triazol-3-yl)-4'-[2-[(2-hydroxy-2-phenylethyl)amino]ethyl]acetanilide dihydrochloride

EXAMPLE 36

(R)-2-(2-Acetamidothiazol-4-yl)-4'-[2-[(2-hydroxy-2-phenylethyl)amino]ethyl]acetanilide hydrochloride

EXAMPLE 37

(R)-4'-[2-[(2-Hydroxy-2-phenylethyl)amino]ethyl]-2-(2-methanesulfonamidothiazol-4-yl)acetanilide hydrochloride

EXAMPLE 38

(R)-2-(2-Guanidinothiazol-4-yl)-4'-[2-[(2-hydroxy-2-phenylethyl)amino]ethyl]acetanilide dihydrochloride

EXAMPLE 39

(R)-4'-[2-[(2-Hydroxy-2-phenylethyl)aminolethyl]-2-(2-phenylaminothiazol-4-yl)acetanilide hydrochloride

EXAMPLE 40

(R)-4'-[2-[(2-Hydroxy-2-phenylethyl)amino]ethyl]-2-[1-(4-nitrobenzyl)-1H-imidazol-2-yl]acetanilide hydrochloride

EXAMPLE 41

To 690 mg of tert-butyl (R)-N-[2-[4-[2-(2-amino-thiazol-4-yl)acetamino]phenyl]ethyl]-N-[(2-hydroxy-2-phenyl)ethyl]carbamate were added 30 ml of methanol and 15 ml of a solution of 4N hydrogen chloride in ethyl acetate, and the mixture was stirred at room temperature for two hours. The solvent was evaporated in vacuo, and the residue was purified by a reverses phase column chromatography (eluent: water/methanol 2/1) to give 310 mg of (R)-2-(2-aminothiazol-4-yl)-4'-[2-(2-hydroxy-2-phenylethyl)amino]-ethyl]acetanilide dihydrochloride.

The compounds of Examples 42 to 57 were prepared by the same manner as in Example 41.

EXAMPLE 42

(R)-4'-[2-[(2-Hydroxy-2-phenylethyl)amino]ethyl]-(2-amino-thiazol-4-yl)carboxanilide hydrochloride

EXAMPLE 43

(R)-2-(2-Amino-5-methylthiazol-4-yl)-4'-2-[(2-hydroxy-2-phenylethyl)amino]ethyl]acetanilide dihydrochloride

EXAMPLE 44

(R)-2-(2-Aminothiazol-4-yl)-2-methyl-4'-[2-[(2-hydroxy-2-phenylethyl)amino]ethyl]propionanilide hydrochloride

EXAMPLE 45

(R)-4'-[2-[(2-Hydroxy-2-phenylethyl)amino]ethyl]-(2-amino-4,5,6,7-tetrahydrobenzothiazol-4-yl)carboxanilide dihydrochloride

EXAMPLE 46

(R)-4'-[2-[(2-Hydroxy-2-phenylethyl)amino]ethyl]-2-(imidazo[2,1-b]thiazol-6-yl)acetanilide hydrochloride

EXAMPLE 47

(R)-2-(2-Benzyl-1H-1,2,4-triazol-3-yl)-4'-[2-[(2-hydroxy-2-phenylethyl)amino]ethyl]acetanilide hydrochloride

EXAMPLE 48

(R)-2-(1-Benzyl-1H-1,2,4-triazol-3-yl)-4'-[2-[(2-hydroxy-2-phenylethyl)amino]ethyl]acetanilide hydrochloride

EXAMPLE 49

(R)-2-(3-Benzyl-2-thioxothiazol-4-yl)-4'-[2-[(2-hydroxy-2-phenylethyl)amino]ethyl]acetanilide hydrochloride

EXAMPLE 50

(R)-4'-[2-[(2-Hydroxy-2-phenylethyl)amino]ethyl]-(5,6,7,8-tetrahydroquinolin-8-yl)carboxanilide dihydrochloride

EXAMPLE 51

(R)-4'-[2-[(2-Hydroxy-2-phenylethyl)amino]ethyl]-2-(1-phenyl-1H-imidazol-2-yl)acetanilide dihydrochloride

EXAMPLE 52

(R)-4'-[2-[(2-Hydroxy-2-phenylethyl)amino]ethyl]-2-[(1-(4-isopropylbenzyl)-1H-imidazol-2-yl) acetanilide dihydrochloride

EXAMPLE 53

(R)-4'-[2-[(2-Hydroxy-2-phenylethyl)amino]ethyl]-2-[(1-(4-phenylbenzyl)-1H-imidazol-2-yl)acetanilide dihydrochloride

EXAMPLE 54

(R)-2-[1-(2-Chlorobenzyl)-1H-imidazol-2-yl]-4'-[2-[(2-hydroxy-2-phenylethyl)amino]ethyl]acetanilide dihydrochloride

EXAMPLE 55

(R)-2-[1-(3-Chlorobenzyl)-1H-imidazol-2-yl]-4'-[2-[(2-hydroxy-2-phenylethyl)amino]ethyl]acetanilide dihydrochloride

EXAMPLE 56

(R)-2-[1-(3,4-Dichlorobenzyl)-1H-imidazol-2-yl]-4'-[2-[(2-hydroxy-2-phenylethyl)amino]ethyl] acetanilide dihydrochloride

EXAMPLE 57

(R)-4'-[2-[(2-Hydroxy-2-phenylethyl)amino]ethyl]-2-[(1-(2-pyridyl)methyl-1H-imidazol-2-yl) acetanilide dihydrochloride The compound of Example 58 was prepared by the same manner as in Example 1.

EXAMPLE 58

(R)-2-(2-aminopyridin-6-yl)-4'-[2-[(2-hydroxy-2-phenyl-ethyl)amino]ethyl]acetanilide dihydrochloride

EXAMPLE 59

To a solution of tert-butyl (R)-N-[2-[4-[[2-(2-amino-thiazol-4-yl)-2-oxoacetyl]amino]phenyl]ethyl]-N-(2-hydroxy-2-phenylethyl) carbamate in 30 ml of methanol was added 130 mg of sodium borohydride at room temperature. The reaction mixture was stirred at room temperature for three hours, and the solvent was evaporated in vacuo. The residue was dissolved in 5 ml of methanol, and to this reaction solution was added 10 ml of a solution of 4N hydrogen chloride-ethyl acetate. The reaction solution was stirred at room temperature for eight hours and the solvent was evaporated in vacuo. The residue was purified by silica gel column chromatography (eluent: chloroform/methanol=5/1). The resulting residue was purified by reversed phase column chromatography (eluent: water/methanol=2/1) to give 77 mg of (R)-2-(2-amino-thiazol-4-yl)-2-hydroxy-4'-[2-(2-hydroxy-2-phenylethyl)-amino]acetanilide hydrochloride.

EXAMPLE 60

To 349 mg of tert-butyl (R)-N-[2-[4-[[2-(2-benzyl-oxypyridin-6-yl)acetyl]amino]phenyl]ethyl]-N-(2-hydroxy-2-phenylethyl) carbamate were added 478 mg of pentamethylbenzene and 5 ml of trifluoroacetic acid successively. The reaction solution was stirred at room temperature for four hours, and the solvent was evaporated in vacuo. To the residue were added water and potassium carbonate to make the solution basic, and the aqueous phase was extracted with a mixed solvent of chloroform and tetrahydrofuran. The organic layer was dried over anhydrous magnesium sulfate, and the solvent was evaporated in vacuo. The residue was purified by silica gel column chromatography (eluent: chloroform/methanol=10/1→5/1). To an ethanolic solution of the resulting residue was added 100 µl of a 4N hydrogen chloride-ethyl acetate solution, and then the solvent was evaporated in vacuo. The resulting crude crystals were recrystallized from ethanol-ethyl acetate to give 65 mg of (R)-2-(2-benzyloxypyridin-6-yl)-4'-[2-[(2-hydroxy-2-phenylethyl)amino]ethyl]acetanilide hydrochloride.

The compounds of Examples 61 to 76, 83 and 85 were prepared by the same manner as in Example 1; and the compounds of Examples 77 to 82 were prepared by the same manner as in Example 41.

EXAMPLE 61

(R)-4'-[2-[(2-Hydroxy-2-phenylethyl)aminolethyl]-2-(2-methylpropyl-1H-imidazol-2-yl)acetanilide dihydrochloride

EXAMPLE 62

(R)-2-[1-(2-Fluorobenzyl)-1H-imidazol-2-yl]-4'-[2-(2-hydroxy-2-phenylethyl)amino]ethyl]acetanilide dihydrochloride

EXAMPLE 63

(R)-[1-(3-Fluorobenzyl)-1H-imidazol-2-yl]-4'-[2-(2-hydroxy-2-phenylethyl)amino]ethyl]acetanilide dihydrochloride

EXAMPLE 64

(R)-2-[1-(2,4-Difluorobenzyl)-1H-imidazol-2-yl]-4'-[2-(2-hydroxy-2-phenylethyl)amino]ethyl] acetanilide dihydrochloride

EXAMPLE 65

(R)-2-[1-(2,6-Difluorobenzyl)-1H-imidazol-2-yl]-4'-[2-(2-hydroxy-2-phenylethyl)amino]ethyl] acetanilide dihydrochloride

EXAMPLE 66

(R)-2-[1-(3,5-Difluorobenzyl)-1H-imidazol-2-yl]-4'-[2-(2-hydroxy-2-phenylethyl)amino]ethyl] acetanilide dihydrochloride

EXAMPLE 67

(R)-2-[1-(2,5-Difluorobenzyl)-1H-imidazol-2-yl])-4'-[2-(2-hydroxy-2-phenylethyl)amino]ethyl] acetanilide dihydrochloride

EXAMPLE 68

(R)-2-[1-(3,4-Difluorobenzyl)-1H-imidazol-2-yl3-4'-[2-(2-hydroxy-2-phenylethyl)amino]ethyl] acetanilide dihydrochloride

EXAMPLE 69

(R)-4'-[2-[(2-Hydroxy-2-phenylethyl)amino]ethyl]-2-[1-(2,3,6-trifluorobenzyl)-1H-imidazol-2-yl] acetanilide dihydrochloride

EXAMPLE 70

(R)-4'-[2-[(2-Hydroxy-2-phenylethyl)amino]ethyl]-2-[1-(2,4,5-trifluorobenzyl)-1H-imidazol-2-yl] acetanilide dihydrochloride

EXAMPLE 71

(R)-4'-[2-[(2-Hydroxy-2-phenylethyl)amino]ethyl]-2-[1-(3,4,5-trifluorobenzyl)-1H-imidazol-2-yl] acetanilide dihydrochloride

EXAMPLE 72

(R)-4'-[2-[(2-Hydroxy-2-phenylethyl)amino]ethyl]-2-[1-(2,3,4,5,6-pentafluorobenzyl)-1H-imidazol-2-yl]acetanilide dihydrochloride

EXAMPLE 73

(R)-4'-[2-[(2-Hydroxy-2-phenylethyl)amino]ethyl]-2-[1-(3-iodobenzyl)-1H-imidazol-2-yl]acetanilide dihydrochloride

EXAMPLE 74

(R)-2-[1-(2,6-Dichlorobenzyl)-1H-imidazol-2-yl]-4'-[(2-hydroxy-2-phenylethyl)amino]ethyl]acetanilide hydrochloride

EXAMPLE 75

(R)-2-[1-(4-Cyanobenzyl)-1H-imidazol-2-yl]-4'-[2-(2-hydroxy-2-phenylethyl)amino]ethyl]acetanilide dihydrochloride

EXAMPLE 76

(R)-4'-[2-[(2-Hydroxy-2-phenylethyl)amino]ethyl]-2-[1-(quinolin-2-yl)-1H-imidazol-2-yl]acetanilide trihydrochloride

EXAMPLE 77

(R)-2-[1-(2-Chloro-6-fluorobenzyl)-1H-imidazol-2-yl]-4'-[2-(2-hydroxy-2-phenylethyl)amino]ethyl] acetanilide

EXAMPLE 78

(R)-2-[1-(2-Chloro-4-fluorobenzyl)-1H-imidazol-2-yl]-4'-[2-(2-hydroxy-2-phenylethyl)amino]ethyl] acetanilide

EXAMPLE 79

(R)-2-[1-(2,5-Dichlorobenzyl)-1H-imidazol-2-yl]-4'-[2-(2-hydroxy-2-phenylethyl)amino]ethyl] acetanilide dihydrochloride

EXAMPLE 80

(R)-4'-[2-[(2-Hydroxy-2-phenylethyl)amino]ethyl]-2-[1-(2,3,4-trifluorobenzyl)-1H-imidazol-2-yl] acetanilide dihydrochloride

EXAMPLE 81

(R)-4'-[2-[(2-Hydroxy-2-phenylethyl)amino]ethyl]-2-[1-(4-methoxycarbonylbenzyl)-1H-imidazol-2-yl] acetanilide dihydrochloride

EXAMPLE 82

(R)-4'-[2-[(2-Hydroxy-2-phenylethyl)amino]ethyl]-2-[1-[(piperidine-1-carbonyl)benzyl]-1H-imidazol-2-yl]acetanilide dihydrochloride

EXAMPLE 83

(R)-4'-[2-[(2-Hydroxy-2-phenylethyl)amino]ethyl]-2-(1-pyrazolyl)acetanilide hydrochloride

EXAMPLE 84

(R)-4'-[2-[(2-Hydroxy-2-phenylethyl)amino]ethyl]-2-(1,2,4-triazol-1-yl)acetanilide dihydrochloride

EXAMPLE 85

(R)-2-(2-Aminobenzimidazol-1-yl)-4'-[(2-[(2-hydroxy-2-phenylethyl)amino]ethyl]acetanilide dihydrochloride

EXAMPLE 86

To a solution of 20.1 g of 4'-[2-[N-benzyl-N-(2-hydroxy-2-phenylethyl)amino]ethyl]-2-(2-pyridyl) acetanilide in 400 ml of methanol was added 5.96 g of 10% palladium-carbon. The reaction solution was stirred for six hours in a hydrogen atmosphere under atmospheric pressure. Insoluble matters were filtered off using Celite and the filtrate was concentrated in vacuo. To a methanolic solution of the resulting residue was added 10.8 ml of a 4N hydrogen chloride-ethyl acetate solution, and the solvent was evaporated in vacuo. The resulting crude crystals were recrystallized from methanol-ethanol to give (R)-4'-[2-[(2-hydroxy-2-phenylethyl)amino]ethyl]-2-(2-pyridyl)acetanilide hydrochloride.

The compounds of 87 to 90 were prepared by the same manner as in Example 86.

EXAMPLE 87

(R)-4'-[2-[(2-Hydroxy-2-phenylethyl)amino]ethyl]-2-(3-pyridyl)acetanilide hydrochloride

EXAMPLE 88

(R)-4'-[2-[(2-Hydroxy-2-phenylethyl)amino]ethyl]-2-(4-pyridyl)acetanilide hydrochloride

EXAMPLE 89

(R)-4'-[2-[(2-Hydroxy-2-phenylethyl)amino]ethyl]-3-(2-pyridyl)propionanilide hydrochloride

EXAMPLE 90

(R)-4'-[2-[(2-Hydroxy-2-phenylethyl)amino]ethyl]-2-[(1-phenylethyl)-1H-imidazol-2-yl]acetanilide dihydrochloride

EXAMPLE 91

(R)-2-(1H-Benzimidazol-2-yl)-4'-[4-[2-[N-benzyl-N-(2-hydroxy-2-phenylethyl)amino]ethyl]phenyl]acetanilide (240 mg) was dissolved in 30 ml of ethanol, then 170 mg of 10% palladium-carbon was added thereto and the mixture was stirred for nine hours in a hydrogen atmosphere under atmospheric pressure. The catalyst was filtered off, the solvent was evaporated in vacuo, and the residue was washed with ethanol-ethyl acetate to give 200 mg of (R)-2-(1H-benzimidazol-2-yl)-4'-[2-[(2-hydroxy-2-phenylethyl)amino]-ethyl]acetanilide.

The compounds of Examples 92 and 93 were prepared by the same manner as in Example 86.

EXAMPLE 92

(R)-4'-[2-[(2-Hydroxy-2-phenylethyl)amino]ethyl]-2-(3-methylpyridin-2-yl]acetanilide hydrochloride

EXAMPLE 93

(R)-4'-[2-[(2-Hydroxy-2-phenylethyl)amino]ethyl]-2-(2-pyrazinyl)acetanilide hydrochloride

EXAMPLE 94

(R)-4'-[4-[2-[N-Benzyl-N-(2-hydroxy-2-phenylethyl)-amino]ethyl]phenyl]-2-(1-benzyl-1H-imidazol-2-yl) acetanilide (350 mg) was dissolved in 20 ml of ethanol, then 130 mg of 10% palladium-carbon was added thereto, and the mixture was stirred for 17.5 hours in a hydrogen atmosphere under atmospheric pressure. The catalyst was filtered off, the solvent was evaporated in vacuo, and the residue was purified by silica gel column chromatography (eluent: chloroform/methanol/concentrated aqueous ammonia=200/10/1). The resulting oily substance was dissolved in methanol, and 280 µl of a 4N hydrogen chloride-ethyl acetate solution was added thereto. The mixture was filtered after adding active carbon was added thereto, and the solvent was evaporated in vacuo to give 200 mg of (R)-2-(1-benzyl-1H-imidazol-2-yl)-4'-[2-[(2-hydroxy-2-phenylethyl)amino] ethyl]acetanilide dihydrochloride.

The compounds of Examples 95 and 97 were prepared by the same manner as in Example 91; the compounds of Examples 98 and 100 were prepared by the same manner as in Example 94; and the compounds of Examples 99 and 101 to 103 were prepared by the same manner as in Example 86.

EXAMPLE 95

(R)-4'-[2-[(2-Hydroxy-2-phenylethyl)amino]ethyl]-2-(4-methyl-2-pyridyl)acetanilide

EXAMPLE 96

(R)-4'-[2-[(2-Hydroxy-2-phenylethyl)amino]ethyl]-2-(5-methyl-2-pyridyl)acetanilide

EXAMPLE 97

(R)-4'-[2-[(2-Hydroxy-2-phenylethyl)amino]ethyl]-2-(6-methyl-2-pyridyl)acetanilide

EXAMPLE 98

4'-[(R)-2-[((R)-2-Hydroxy-2-phenylethyl)amino] propyl]-2-(2-pyridyl)acetanilide hydrochloride

EXAMPLE 99

4'-[(S)-2-[((R)-2-Hydroxy-2-phenylethyl) aminolpropyl]-2-(2-pyridyl)acetanilide hydrochloride

EXAMPLE 100

2-(1-Benzyl-1H-imidazol-2-yl)-4'-[(S)-2-[((R)-2-hydroxy-2-phenylethyl)amino]propyl]acetanilide hydrochloride

EXAMPLE 101

4'-[2-[[2-Hydroxy-2-(2-fluorophenyl)ethyl]amino] ethyl]-2-(2-pyridyl)acetanilide hydrochloride

EXAMPLE 102

4'-[2-[[2-Hydroxy-2-(3-fluorophenyl)ethyl]amino] ethyl]-2-(2-pyridyl)acetanilide hydrochloride

EXAMPLE 103

4'-[2-[[2-Hydroxy-2-(4-fluorophenyl)ethyl]amino]
ethyl]-2-(2-pyridyl)acetanilide hydrochloride

EXAMPLE 104

To a solution of 805 mg of 4'-cyanomethyl-2-(2-pyrimidinyl)acetanilide in 30 ml of tetrahydrofuran were added 30 ml of an ethanolic solution of a Raney nickel and 3 ml of concentrated aqueous ammonia. The reaction solution was stirred for four hours in a hydrogen atmosphere under atmospheric pressure, then insoluble matters were filtered off using Celite, and the solvent was evaporated. To the resulting residue were added 10 ml of 2-propanol, 300 mg of (R)-styrene oxide and 2 ml of methanol successively. The reaction mixture was heated to reflux for ten hours, and the solvent was evaporated. The residue was purified by silica gel column chromatography (eluent: chloroform/methanol=10/1). To a methanolic solution of the resulting residue was added 150 μl of 4N hydrogen chloride-ethyl acetate solution, and the solvent was evaporated in vacuo. The resulting residue was crystallized from methanol-ethanol-ethyl acetate and then recrystallized from ethanol-diethyl ether to give 160 mg of (R)-4'-[2-[(2-hydroxy-2-phenylethyl)amino]ethyl]-2-(2-pyrimidinyl]acetanilide hydrochloride.

The compounds of Examples 105 to 108 were prepared by the same manner as in Example 104; and the compound of Example 109 was prepared by the same manner as in Example 91.

EXAMPLE 105

(R)-4'-[2-[(2-Hydroxy-2-phenylethyl)amino]ethyl]-2-(2-quinolyl)acetanilide hydrochloride

EXAMPLE 106

(R)-4'-[2-[[2-Hydroxy-2-(3-chlorophenyl)ethyl]amino]-ethyl]-2-(2-pyridyl)acetanilide hydrochloride

EXAMPLE 107

4'-[2-[[2-Hydroxy-2-(3-pyridyl)ethyl]amino]ethyl]-2-(2-pyridyl)acetanilide hydrochloride

EXAMPLE 108

(R)-2-[1-(4-Chlorobenzyl)-1H-benzimidazol-2-yl]-4'-[2-[(2-hydroxy-2-phenylethyl)amino]ethyl]
acetanilide dihydrochloride

EXAMPLE 109

(R)-2-(4,6-Dimethyl-2-pyridyl)-4'-[2-[(2-hydroxy-2-phenylethyl)amino]ethyl]acetanilide

EXAMPLE 110

To 4'-(3-aminopropyl)-2-(2-pyridyl)acetanilide were added 10 ml of 2-propanol and 600 mg of (R)-styrene oxide successively. The reaction mixture was heated to reflux for four hours, and the solvent was evaporated. The residue was purified by silica gel column chromatography (eluent: chloroform/methanol=30/1Δ10/1). To a methanolic solution of the resulting residue was added 100 μl of a 4N hydrogen chloride-ethyl acetate solution, and the solvent was evaporated in vacuo. The resulting crude crystals were recrystallized from ethanol-diethyl ether to give 71 mg of (R)-4'-[3-[(2-hydroxy-2-phenylethyl)aminolpropyl]-2-(2-pyridyl)acetanilide hydrochloride.

EXAMPLE 111

To a solution of 3.62 g of tert-butyl N-[2-[4-[[2-(2-pyridyl)acetyl]amino]phenoxy]ethyl]carbamate in 30 ml of methanol was added 50 ml of a 4N hydrochloride-ethyl acetate solution. After the reaction solution was stirred at room temperature for eight hours, the solvent was evaporated in vacuo. To the residue were added an aqueous solution of sodium hydrogen carbonate and potassium carbonate to adjust to pH about 12. The resulting aqueous phase was extracted with a mixed solvent of chloroform and tetrahydrofuran. The organic layer was dried over anhydrous magnesium sulfate and concentrated, the resulting residue was dissolved in 40 ml of methanol, and 1.02 g of (R)-styrene oxide was added thereto. After the reaction solution was heated to reflux for 26 hours, the solvent was evaporated in vacuo. The resulting residue was purified by silica gel column chromatography (eluent: chloroform/methanol=30/1→10/1) and dissolved in methanol, 0.59 ml of a 4N hydrogen chloride-ethyl acetate solution was added, and the solvent was evaporated in vacuo. The resulting crude crystals were recrystallized from methanol-ethanol to give 320 mg of (R)-4'-[2-[(2-hydroxy-2-phenylethyl)-amino]ethoxy]-2-(2-pyridyl)acetanilide hydrochloride

EXAMPLE 112

To a solution of 490 mg of tert-butyl N-[1,1-di-methyl-2-[4-[[2-(2-pyridyl)acetyl]amino]phenyl]ethyl]-carbamate in 10 ml of methanol was added 30 ml of a 4N hydrochloride-ethyl acetate solution. After the reaction solution was stirred at room temperature for eight hours, the solvent was evaporated in vacuo. To the residue were added an aqueous solution of sodium hydrogen carbonate and potassium carbonate to adjust to pH about 12. The resulting aqueous phase was extracted with a mixed solvent of chloroform and tetrahydrofuran. The organic layer was dried over anhydrous magnesium sulfate and concentrated, the resulting residue was dissolved in 2 ml of 2-propanol and 2 ml of methanol, and 120 mg of (R)-styrene oxide was added thereto. After the reaction solution was heated to reflux for 24 hours, the solvent was evaporated in vacuo. The resulting residue was purified by silica gel column chromatography (eluent: chloroform/methanol=30/1→15/1) and dissolved in methanol, 0.1 ml of a 4N hydrogen chloride-ethyl acetate solution was added, and the solvent was evaporated in vacuo. The resulting residue was purified by silica gel column chromatography (eluent: chloroform/methanol=5/1) and a reversed phase column chromatography (eluent: water/methanol=2/1→1/1) to give 35 mg of (R)-4'-[2,2-dimethyl-2-[(2-hydroxy-2-phenylethyl)amino]ethyl]-2-(2-pyridyl)acetanilide hydrochloride.

The compound of Example 113 was prepared by the same manner as in Example 1.

EXAMPLE 113

(R)-1-(4-[2-[(2-Hydroxy-2-phenylethyl)amino]ethyl]
phenyl]-3-(2-pyridyl)urea dihydrochloride As hereunder, physical and chemical properties of the compounds of the Referential Examples are given in Tables 1 and those of the compounds of the Examples are given in Tables 2.

The symbols in the tables have the following meanings.

Rex.: Referential Example No.

Ex.: Example No.

DATA: Physico-chemical properties

NMR: Nucleomagnetic resonance spectrum (TMS internal standard; DMSO-d was used as a solvent unless otherwise specified)

mp: melting point dec: decomposition

MS (m/z): mass spectrographic data (m/z)

Structure: structural formula

TABLE 1

| Rex. | DATA |
|---|---|
| 1 | NMR (CDCl$_3$) δ: 2.75(1H, dd, J=12.4, 8.8Hz), 2.85–3.04 (5H, m), 4.70(1H, dd, J=8.8, 3.7Hz), 7.24–7.40(7H, m), 8.10–8.20 (2H, m) |
| 2 | NMR (CDCl$_3$) δ: 1.44(9H, s), 2.75–3.10(2H, m), 3.20–3.70 (4H, m), 4.93(1H, br), 7.25–7.40(7H, m), 8.14(2H, d, J=8.4Hz) |
| 3 | NMR (CDCl$_3$) δ: 1.47(9H, s), 2.55–2.80(2H, m), 3.20–3.40 (2H, m), 3.45–3.65(2H, m), 4.87(1H, m), 6.57–6.65(2H, m), 6.83–7.04(2H, m), 7.25–7.40(5H, m) |
| 4 | NMR (CDCl$_3$) δ: 1.47(9H, s), 2.62–2.93(2H, m), 3.14–3.58 (4H, m), 4.35(1H, brs), 4.90(1H, br), 7.06–7.40(7H, m), 7.45–7.50 (1H, m), 7.67–7.72(2H, m), 7.90(1H, dt, J=2.0, 8.0Hz), 8.25–8.31 (1H, m), 8.58–8.63(1H, m), 9.98(1H, brs) |
| 5 | NMR (CDCl$_3$) δ: 1.49(9H, s), 2.64–2.90(2H, m), 3.16–3.60 (4H, m), 4.38(1H, brs), 4.91(1H, br), 7.10–7.42(7H, m), 7.55(1H, dd, J=8.0, 4.4Hz), 7.74(1H, t, J=8.0Hz), 7.77–7.84(2H, m), 8.01(1H, d, J=8.0, 1.2Hz), 8.34(1H, d, J=8.4, 1.6Hz), 8.96(1H, d, J=7.6, 1.6Hz), 9.02(1H, d, J=4.4, 2.0Hz), 13.61(1H, brs) |

TABLE 1-continued

| Rex. | DATA |
|---|---|
| 6 | NMR (CDCl$_3$) δ: 1.47(9H, s), 2.60–2.80(2H, m), 3.15–3.55 (4H, m), 3.78(2H, s), 4.36(1H, brs), 4.82–4.94(1H, m), 5.18 (2H, s), 6.92–6.99(2H, m), 7.00–7.13(5H, m), 7.25–7.38 (6H, m), 7.42–7.48(2H, m), 10.34(1H, brs) |
| 7 | NMR (CDCl$_3$) δ: 2.56–2.94(6H, m), 3.40–3.65(2H, m), 3.80(1H, brs), 3.95(1H, d, 13.6Hz), 4.62(1H, dd, J=10.0, 3.2Hz), 6.57–6.66(2H, m), 6.87–6.98(2H, m), 7.20–7.37(10H, m) |
| 8 | NMR (CDCl$_3$) δ: 2.40(3H, s), 2.54–3.00(6H, m), 3.57(1H, d, J=13.6Hz), 3.88(2H, s), 3.95(1H, d, J=13.6Hz), 4.62(1H, dd, J=10.4, 3.6Hz), 7.00–7.75(16H, m), 8.44(1H, d, J=4.4Hz), 9.66(1H, brs) |
| 9 | NMR (CDCl$_3$) δ: 2.58–2.65(1H, m), 2.75–3.00(5H, m), 3.59(1H, d, J=13.2Hz), 3.95(1H, d, J=13.2Hz), 5.01(1H, dd, J=10.0, 3.2Hz), 6.97–7.03(1H, m), 7.12–7.35(9H, m), 7.48–7.56(1H, m), 8.04–8.13(2H, m) |
| 10 | NMR (CDCl$_3$) δ: 3.70(2H, s), 3.88(2H, s), 7.23–7.32 (4H, m), 7.54–7.62(2H, m), 7.71(1H, dt, J=7.6, 1.6Hz), 8.63(1H, d), 10.04(1H, brs) |
| 11 | NMR (CDCl$_3$) δ: 2.26(3H, s), 2.39(3H, s), 2.57(2H, t, J=7.2Hz), 2.72(2H, t, J=7.2Hz), 3.72(2H, s), 6.95(1H, s), 7.01(1H, s), 7.11(2H, d, J=8.8Hz), 7.51(2H, d, J=8.8Hz), 10.17(1H, s) |
| 12 | NMR δ: 2.32(3H, s), 2.41(3H, s), 2.90–3.19(6H, m), 3.75(2H, s), 4.01(2H, s), 4.89(1H, dt, J=7.6, 3.2Hz), 6.99–7.71(16H, m), 10.26(1H, s) |

TABLE 2

| Ex. | DATA |
|---|---|
| 1 | mp: 223–225° C., NMR δ: 2.95–3.28(6H, m), 4.98–5.07(1H, m), 7.23–7.44(6H, m), 7.65–7.75(1H, m), 7.88(2H, d, J= 8.4Hz), 8.05–8.22(2H, m), 8.75(1H, d, J=4.4Hz), 8.97(1H, brs), 9.43(1H, brs), 10.65(1H, brs) |
| 2 | mp: 263–265° C., NMR δ: 2.92–3.10(3H, m), 3.13–3.27(3H, m), 5.00(1H, dd, J=10.8, 2.8Hz), 7.24–7.44(8H, m), 7.74–7.81(3H, m), 8.57(1H, d, J=8.0Hz), 8.81–8.96(2H, m), 9.20–9.30(2H, m), 10.71(1H, brs) |
| 3 | mp: 145–147° C., NMR δ: 2.94–3.10(3H, m), 3.14–3.30(3H, m), 4.97–5.05(1H, m), 7.27–7.46(7H, m), 7.77–7.90(4 H, m), 8.30(1H, dd, J=8.4, 1.6Hz), 8.60–8.71(2H, m), 8.89(1H, brs), 9.10–9.30(2H, m), 13.12(1H, brs) |
| 4 | mp: 246–248° C. (dec), NMR δ: 2.92–3.09(3H, m), 3.11–3.26(3H, m), 5.01(1H, dd, J=10.4, 2.8Hz), 7.24(2H, d, J= 8.4Hz), 7.29–7.47(6H, m), 7.56–7.75(4H, m), 7.85(1H, d, J=8.0Hz), 8.11(1H, t, J=7.6Hz), 8.73(1H, d, J=4.4Hz), 8.92 (1H, brs), 9.32(1H, brs), 10.69(1H, brs) |
| 5 | mp: 228–233° C. (dec), NMR δ: 2.88–3.09(3H, m), 3.10–3.24(3H, m), 4.30(2H, s), 4.93–5.01(1H, m), 6.19(1H, d, J= 3.6Hz), 7.18–7.27(2H, m), 7.28–7.53(7H, m), 7.57–7.62(2H, m), 7.97(1H, d, J=7.6Hz), 8.08(1H, d, J=8.0Hz), 8.83(1H, brs), 9.11(1H, brs), 10.57(1H, brs) |
| 6 | mp: 161–162° C., NMR δ: 2.86–3.24(6H, m), 4.2492H, s), 4.97(1H, dd, J=9.6, 2.8Hz), 7.16–7.23(2H, m), 7.27–7.44 (5H, m), 7.55(1H, s), 7.61(2H, d, J=8.4Hz), 7.85(1H, s), 8.27(1H, d, J=2.4Hz), 8.97(1H, brs), 9.47(1H, brs), 10.94(1H, brs) |
| 7 | NMR δ: 2.70(3H, s), 2.86–3.27(6H, m), 3.85(2H, s), 5.00–5.05(1H, m), 7.18–7.60(10H, m), 10.43(1H, s) |
| 8 | mp: 203–207° C., NMR δ: 2.92–3.08(3H, m), 3.10–3.22(3H, m), 4.28(2H, s), 5.01(1H, d, J=7.8Hz), 6.21(1H, brs), 7.22(2H, d, J=8.3Hz), 7.25–7.63(4H, m), 8.93(1H, brs), 9.38(1H, brs), 10.86(1H, s) |
| 9 | mp: 259–261° C., NMR δ: 2.90–3.10(3H, m), 3.10–3.25(3H, m), 4.15(2H, s), 4.97(1H, d, J=10.8Hz), 6.20(1H, d, J= 3.9Hz), 7.21(sH, 3, J=8.8Hz), 7.30–7.42(5H, m), 7.57(2H, d, J=8.8Hz), 8.85(1H, brs), 9.14(1H, brs), 10.58(1H, s) |
| 10 | mp: 210–213° C., NMR δ: 2.86–3.08(3H, m), 3.12–3.22(3H, m), 3.73(2H, s), 4.91–4.98(1H, m), 6.19(1H, d, J=3.9Hz), 7.21(2H, d, J=8.3Hz), 7.29–7.42(5H, m), 7.54(2H,d, J=8.3Hz), 8.78(1H, brs), 8.99(1H, brs), 10.35(1H, s), 13.21(1H, brs), 13.34(1H, brs) |
| 11 | mp: 205–210° C. (dec), NMR δ: 2.90–3.25(6H, m), 4.95–5.04(1H, m), 7.23–7.44(7H, m), 7.67–7.75(2H, m), 8.15(1 H, s), 8.88(1H, brs), 9.25(1H, brs) |
| 12 | mp: 244–246° C., NMR δ: 2.90–3.08(3H, m), 3.10–3.20(3H, m), 3.67(2H, s), 5.00(1H, dd, J=24, 10.02Hz), 7.192H, d, J=8.3Hz), 7.28–7.42(5H, m), 7.57(2H, d, J=8.3Hz), 8.90(1H, s), 9.31(1H, s), 10.31(1H, s) |
| 13 | mp: 205–208° C., NMR δ: 1.27(3H, t, J=7.1Hz), 2.88–3.08(3H, m), 3.12–3.22(3H, m), 3.86(2H, s), 4.27(2H, q, J=7.1 Hz), 4.96(1H, d, J=8.3Hz), 6.20(1H, s), 7.19(2H, d, J=8.3Hz), 7.30–7.42(5H, m), 7.57(2H, d, J=8.3Hz), 8.81(1H, s), 9.10(1H, s), 10.33(1H, s), 12.53(1H, s) |

TABLE 2-continued

| Ex. | DATA |
|---|---|
| 14 | mp: 169–173° C., NMR δ: 2.88–3.22(6H, m), 3.66(2H, s), 4.98(1H, dd, J=2.9, 13.1Hz), 6.72(1H, s), 7.19(2H, d, J= 8.3Hz), 7.23–7.42(8H, m), 7.59(2H, d, J=8.3Hz), 7.72–7.78(1H, m), 8.85(1H, s), 9.18(1H, brs), 10.24(1H, brs), 10.55 (1H, s) |
| 15 | mp: 248–251° C., NMR δ: 2.90–3.08(3H, m), 3.09–3.21(3H, m), 3.88(2H, s), 5.02(1H, dd, J=10.0, 2.4Hz), 6.20(1H, brs), 7.16–7.22(2H, m), 7.28–7.46(7H, m), 7.57–7.63(2H, m), 7.84(1H, t, J=7.2Hz), 8.95(1H, brs), 9.40(1H, brs), 10.48 (1H, brs) |
| 16 | mp: 237–238° C., NMR δ: 2.87–3.24(6H, m), 3.77(2H, s), 4.93–5.03(1H, m), 5.32(2H, s), 6.20(1H, d, J=4.0Hz), 6.73 (1H, d, J=8.0Hz), 6.99(1H, d, J=7.2Hz), 7.16–7.22(2H, m), 7.25–7.46(10H, m), 7.57–7.63(2H, s), 7.67(1H, dd, J=8.4, 7.2Hz), 8.87(1H, brs), 9.24(1H, brs), 10.30(1H, brs) |
| 17 | mp: 190–193° C., NMR δ: 1.68(3H, m), 2.90–3.10(3H, m), 3.10–3.20(3H, m), 4.32(2H, s), 4.67(1H, s), 4.83(2H, s), 4.94(1H, s), 4.99(1H, d, J=8.3Hz), 6.21(1H, brs), 7.21(2H, d, J=8.7Hz), 7.24–7.42(5H, m), 7.56(2H, d, J=8.8Hz), 7.66 (2H, d, J=1.9Hz), 7.71(1H, d, J=1.9Hz), 8.89(1H, brs), 9.30(1H, brs), 10.92(1H, s) |
| 18 | mp: 139–141° C., NMR δ: 3.01(3H, brs), 3.15(3H, brs), 3.92(2H, s), 5.05(1H, d, J=10.3Hz), 5.44(2H, s), 6.19(1H, brs), 7.19(2H, d, J=8.3Hz), 7.31–7.47(10H, m), 7.60(2H, d, J=8.3Hz), 7.66(1H, s), 9.05(1H, brs), 9.35(1H, s), 9.60(1H, brs), 10.76(1H, s) |
| 19 | mp: 140–143° C., NMR δ: 2.99–3.09(3H, m), 3.16(3H, brs), 3.95(2H, s), 5.06(1H, d, J=10.4Hz), 5.57(1H, s), 6.19(1H, brs), 7.19(2H, d, J=8.6Hz), 7.29–7.35(1H, m), 7.37–7.48(8H, m), 7.55–7.57(1H, m), 7.61(2H, d, J=8.6Hz), 9.09(1H, brs), 9.31(1H, d, J=1.5Hz), 9.65(1H, brs), 10.79(1H, s) |
| 20 | mp: 140–143° C., NMR δ: 3.01–3.09(3H, m), 3.16(3H, brs), 3.93(2H, s), 5.06(1H, d, J=10.3Hz), 5.47(2H, s), 6.15 (1H, brs), 7.19(2H, d, J=8.6Hz), 7.29–7.33(1H, m), 7.38–7.46(7H, m), 7.61(2H, d, J=8.6Hz), 7.63(1H, s), 7.70(1H, s), 9.08 (1H, brs), 9.38(1H, s), 9.63(1H, brs), 10.78(1H, s) |
| 21 | mp: 141–146° C., NMR δ: 2.96–3.14 (3H, m), 3.15(3H, brs), 3.91(2H, s), 5.04(1H, d, J=10.3Hz), 5.45(2H, s), 6.22 (1H, brs), 7.19(2H, d, J=8.6Hz), 7.29–7.42(6H, m), 7.50(3H, s), 7.59(2H, d, J=8.6Hz), 7.65(1H, s), .02(1H, brs), 9.32 (1H, d, J=1.5Hz), 9.55(1H, brs), 10.73(1H, s) |
| 22 | mp: 230–235° C., NMR δ: 2.59–3.10(3H, m), 3.10–3.25(3H, m), 4.47(2H, s), 5.01(1H, dd, J=10.3, 2.4Hz), 5.45(2H, s), 6.21(1H, brs), 7.16–7.22(4H, m), 7.28–7.50(7H, m), 7.54(2H, d, J=8.3Hz), 7.68(2H, dd, J=5.8, 1.9Hz), 8.94(1H, brs), 9.42(1H, brs), 10.98(1H, s) |
| 23 | mP: 203–209° C., NMR δ: 2.90–3.10(3H, m), 3.10–3.20(3H, m), 4.41–4.48(2H, s), 4.95–5.05(1H, m), 5.46(2H, s), 6.21(1H, brs), 7.20(2H, d, J=8.6Hz), 7.30–7.42(6H, m), 7.50–7.54(2H, m), 7.70(2H, s), 8.92(1H, brs), 9.39(1H, brs), 10.88–10.95(1H, m) |
| 24 | mp: 221–223° C., NMR δ: 2.90–3.08(3H, m), 3.10–3.22(3H,m), 4.04(2H, s), 4.97(1H, d, J=9.1Hz), 5.44(2H, s), 6.20 (1H, brs), 7.20(2H, d, J=8.1Hz), 7.30–7.41(9H, m), 7.49(2H, d, J=8.6Hz), 7.55(2H, d, J=8.6Hz), 8.83(1H, brs), 9.16 (1H, brs), 10.76(1H, s) |
| 25 | mp: 222–225° C., NMR δ: 2.60–3.05(3H, m), 3.10–3.20(3H, m), 4.43(2H, s), 5.01(1H, d, J=7.6Hz), 5.44(2H, s), 6.21 (1H, brs), 7.15–7.23(4H, m), 7.26–7.46(5H, m), 7.51(2H, d, J=8.8Hz), 7.65–7.72(4H, m), 8.94(1H, brs), 9.41(1H, brs), 10.93(1H, s), 14.72(1H, brs) |
| 26 | mp: 197–203° C., NMR δ: 2.80–3.10(3H, m), 3.10–3.25(3H, m), 4.44(2H, s), 4.99(1H, d, J=8.0Hz), 5.61(2H, s), 6.21 (1H, brs), 7.17(2H, d, J=8.6Hz), 7.30–7.42(5H, m), 7.48(2H, d, J=8.5Hz), 7.54(2H, d, J=8.0Hz), 7.70(2H, d, J=8.1Hz), 7.72–7.77(2H, m), 8.90(1H, brs), 9.34(1H, brs), 10.90(1H, s) |
| 27 | mp: 208–214° C., NMR δ: 2.90–3.10(3H, m), 3.10–3.22(3H, m), 4.44(2H, s), 4.97(1H, d, J=9.7Hz), 5.62(2H, s), 6.20 (1H, brs), 7.16(2H, d, J=8.0Hz), 7.30–7.55(10H, m), 7.70–7.94(6H, m), 8.82(1H, brs), 9.14(1H, brs), 10.76(1H, s) |
| 28 | mp: 219–223° C., NMR δ: 2.11(3H, s), 2.92–3.08(3H, m), 3.10–3.20(3H, m), 4.43(2H, s), 5.02(1H, dd, J=10.2, 2.4 Hz), 5.51(2H, s), 6.22(1H, brs), 7.14–7.34(7H, m), 7.36–7.42(4H, m), 7.48–7.53(3H, m), 8.95(1H, brs), 9.43(1H, brs), 10.94 (1H, s), 14.61(1H, brs) |
| 29 | mp: 204–207° C., NMR δ: 2.24(3H, s), 2.80–3.10(3H, m), 3.10–3.50(3H, m), 4.43(2H, s), 5.01(1H, dd, J=10.3, 2.5Hz), 5.39(2H, s), 6.21(1H, brs), 7.17–7.24(2H, m), 7.47(2H, dd, J=8.8, 5.4Hz), 7.552H, d, J=8.3Hz), 8.94(1H, brs), 9.40(1H, brs), 11.00(1H, s), 14.70(1H, brs) |
| 30 | mp: 225–228° C., NMR δ: 2.90–3.07(3H, m), 3.10–3.23(3H, m), 4.28(2H, s), 4.97(1H, d, J=10.3Hz), 5.68(2H, s), 6.20(1H, d, J=3.4Hz), 7.16–7.23(4H, m), 7.30–7.46(7H, m), 7.53(2H, d, J=8.8Hz), 8.82(1H, brs), 9.11(1H, brs), 10.63(1H, s) |
| 31 | mp: 232–235° C., NMR δ: 2.90–3.10(3H,m), 3.10–3.25(3H, m), 4.03(2H, s), 4.98(1H, d, J=10.3Hz), 5.97(2H, s), 6.20(1H, brs), 7.19(2H, d, J=8.3Hz), 7.29–7.42(6H, m), 7.55(2H, d, J=8.3Hz), 7.67–7.77(2H, m), 8.87(1H, brs), 9.22(1H, brs), 10.49(1H, s), 14.61(1H, brs) |
| 32 | mp: 233–235° C., NMR δ: 2.09–3.10(3H, m), 3.10–3.25(3H, m), 4.01(2H, s), 4.98(1H, d, J=10.3Hz), 5.91(2H, s), 6.19(1H, brs), 7.17–7.48(11H, m), 7.55(2H, d, J=8.3Hz), 8.85(1H, brs), 9.18(1H, brs), 10.47(1H, s) |
| 33 | mp: 240–242° C., NMR δ: 2.90–3.10(3H, m), 3.10–3.25(3H, m), 4.32(2H, s), 4.98(1H, dt, J=10.3, 3.4Hz), 5.72(2H, s), 6.20(1H, d, J=3.9Hz), 7.20(2H, d, J=8.3Hz), 7.30–7.40(6H, m), 7.51(2H, d, J=8.8Hz), 7.62(1H, d, J=8.3Hz), 7.67 (1H, d, J=2.0Hz), 8.86(1H, brs), 9.17(1H, brs), 10.67(1H, s) |
| 34 | mp: 221–224° C., NMR δ: 2.90–3.07(3H, m), 3.10–3.20(3H, m), 4.05(2H, s), 5.00(2H, dd, J=2.7, 10.2Hz), 7.21(2H, d, J=8.6Hz), 7.29–7.42(5H,m), 7.58(2H, d, J=8.6Hz), 8.83(1H, s), 8.91(1H, brs), 9.32(1H, brs), 10.62(1H, s) |
| 35 | mp: 222–224° C., NMR δ: 2.89–3.07(3H, m), 3.12–3.21(3H, m), 3.84(2H, s), 4.33(2H, s), 4.98(1H, dd, J=2.4, 10.2 Hz), 7.20(2H, d, J=8.3Hz), 7.22–7.42(10H, m), 7.58(2H, d, J=8.3Hz), 8.87(1H, brs), 9.22(1H, brs), 10.44(1H, s) |
| 36 | mp: 242–245° C., NMR δ: 2.11(3H, s), 2.99–3.06(3H, m), 3.09–3.21(3H, m), 3.68(2H, s), 5.00(1H, dd, J=2.1, 10.2Hz), 6.02(1H, brs), 6.98(1H, s), 7.18(2H, d, J=8.1Hz), 7.28–7.42(5H, m), 7.58(2H, d, J=8.1Hz), 8.89(1H, brs), 9.30(1H, brs), 10.25(1H, s), 12.10(1H, s) |
| 37 | mp: 252–256° C., NMR δ: 2.89(3H, s), 2.91–3.07(3H, m), 3.11–3.21(3H, m), 3.65(2H, s), 4.95–5.02(1H, m), 6.20 (1H, brs), 6.58(1H, s), 7.20(2H, d, J=8.6Hz), 7.28–7.42(5H, m), 7.57(2H, d, J=8.6Hz), 8.87(1H, brs), 9.24(1H, brs), 10.39 (1H, s), 12.56(1H, s) |
| 38 | mp: >230° C. (dec.), NMR δ: 2.88–3.22(6H,m), 3.73(2H, s), 3.65(2H, s), 5.00(1H, dd, J=2.0, 10.0Hz), 6.20(1H, brs), 7.12(1H, s), 7.18(2H, d, J=8.8Hz), 7.28–7.42(5H, m), 7.59(2H, d, J=8.8Hz), 8.39(4H, brs), 8.91(1H, brs), 9.32(1H, brs), 10.41(1H, s), 12.60(1H, s) |
| 39 | mp: 177–181° c., NMR δ: 2.90–3.10(3H, m), 3.10–3.25(3H, m), 3.67(2H, s), 5.00(1H, dd, J1=10.0, 2.0Hz), 6.68 (1H, s), 6.97(1H, t, J=7.2Hz), 7.19(2H, d, J=8.4Hz), 7.27–7.42(9H, m), 7.59(2H, d, J=8.0Hz), 8.90(1H, brs), 9.29(1H, brs), 10.29(1H, s), 10.54(1H, brs) |
| 40 | mp: 237–243° C., NMR δ: 2.90–3.06(3H, m), 3.06–3.20(3H, m), 4.45(2H, s), 5.01(1H, dd, J=7.8, 2.0Hz), 5.70(2H, s), 6.21(1H, brs), 7.14(2H, d, J=8.8Hz), 7.29–7.42(5H, m), 7.46(2H, d, J=8.8Hz), 7.54(2H, d, J=8.8Hz), 7.77(2H, dd, J=14.4, 2.0Hz), 8.13(2H, d, J=8.4Hz), 8.94(1H, brs), 9.41(1H, brs), 10.95(1H, s) |

TABLE 2-continued

| Ex. | DATA |
|---|---|
| 41 | mp: 151–159° C., NMR δ: 2.90–3.10(3H, m), 3.10–3.20(3H, m), 3.76(2H, s), 5.02(1H, dd, J=10.2, 2.7Hz), 6.70(1H, s), 7.20(2H, d, J=8.8Hz), 7.25–7.40(5H, m), 7.59(2H, d, J=8.8Hz), 8.96(1H, brs), 9.21(1H, brs), 9.43(1H, brs), 10.58 (1H, s) |
| 42 | mp: 205–209° C., NMR δ: 2.90–3.08(3H, m), 3.13–3.23(3H, m), 4.92–4.97(1H, m), 6.20(1H, brs), 7.19–7.42(10H, m), 7.71(2H, d, J=8.8Hz), 8.76(1H, brs), 8.92(1H, brs), 9.65(1H, s) |
| 43 | NMR δ: 2.20(3H, s), 2.90–3.07(3H, m), 3.10–3.20(3H, m), 3.74(2H, s), 5.00(1H, dd, J=2.5, 10.3Hz), 7.20(2H, d, J=8.8 Hz), 7.28–7.42(5H, m), 7.59(2H, d, J=8.8Hz), 8.91(1H, brs), 9.13(1H, brs), 9.33(1H, brs), 10.58(1H, s) |
| 44 | NMR δ: 1.48(6H, s), 2.86–3.22(6H,m ), 4.90–4.96(1H, m), 6.19(1H, brs), 6.40(1H, brs), 7.17(2H, d, J=8.8Hz), 7.27–7.41(5H, m), 7.56(2H, d, J=8.8Hz), 8.74(1H, brs), 8.90(1H, brs), 9.53(1H, s) |
| 45 | NMR δ: 1.68–2.12(4H,m), 2.43–2.59(2H, m), 2.91–3.07(3H, m), 3.11–3.20(3H, m), 3.76–3.81(1H, m), 5.00(1H, d, J= 2.5, 10.3Hz), 6.20(1H, brs), 7.19(2H, d, J=8.3Hz), 7.27–7.42(5H, m), 7.60(1H, d, J=8.3Hz), 8.90(1H, brs), 9.33(1H, brs), 10.43(1H, s) |
| 46 | NMR δ: 2.88–3.24(6H, m), 3.83(2H, s), 4.95–5.04(1H, m), 6.19(1H, brs), 7.16–7.22(2H, m), 7.26–7.45(6H, m), 7.55–7.63(2H, m), 7.87(1H, m), 8.04(1H, d, J=3.6Hz), 8.91(1H, brs), 9.32(1H, brs), 10.42(1H, brs) |
| 47 | MS (m/z): 456[(M+H)$^+$], NMR δ: 2.84–3.19(6H, m), 4.03(2H, s), 4.87–4.97(1H, m), 5.43(2H, s), 6.12(2H, s), 7.20 (2H, d, J=8.3Hz), 7.25–7.41(11H, m), 7.53(2H, d, J=8.3Hz), 7.90(1H, s), 10.38(1H, s) |
| 48 | NMR δ: 2.88–3.18(6H, m), 3.69(2H, s), 4.87–4.95(1H, m), 5.36(2H, s), 6.15–6.21(1H, m), 7.18(2H, d, J=8.3Hz), 7.27–7.41(11H, m), 7.54(2H, d, J=8.3Hz), 8.57(1H, s), 8.72(1H, brs), 8.82(1H, brs), 10.20(1H, s) |
| 49 | NMR δ: 2.88–3.07(3H, m), 3.11–3.21(3H, m), 3.67(2H, s), 4.93–4.99(1H, m), 5.53(2H, s), 6.20(1H, d, J=3.9Hz), 7.00 (1H, s), 7.13(2H, d, J=7.3Hz), 7.18(2H, d, J=8.3Hz), 7.24–7.42(8H, m), 7.49(2H, d, J=8.3Hz), 8.82(1H, brs), 9.11(1H, brs), 10.35(1H, s) |
| 50 | NMR δ: 1.76–1.87(2H, m), 2.18–2.26(2H, m), 2.80–3.22(8H, m), 4.39–4.47(1H, m), 4.95–5.07(1H, m), 7.15–7.22(2H, m), 7.27–7.43(5H, m), 7.54–7.63(2H, m), 7.74–7.82(1H, m), 8.27(1H, d, J=7.2Hz), 8.67(1H, d, J=4.8Hz), 8.97(1H, brs), 9.47(1H, brs), 10.74(1H, brs) |
| 51 | NMR δ: 2.90–3.10(3H, m), 3.10–3.20(3H, m), 4.18(2H, s), 4.96(1H, d, J=8.0Hz), 6.20(1H, brs), 7.18(2H, d, J=8.6Hz), 7.20–7.60(12H, m), 7.84(1H, s), 7.97(1H, s), 8.83(1H, brs), 9.17(1H, brs), 10.55(1H, s) |
| 52 | NMR δ: 1.14(6H, d, J=12.9Hz), 2.83(1H, sep, J=12.9Hz), 2.90–3.22(6H, m), 4.38(2H, s), 4.97(1H, d, J=4.1Hz), 5.39 (2H, s), 6.20(1H, brs), 7.07–7.42(10H, m), 7.52(2H, d, J=8.8Hz), 7.67(2H, d, J=3.9Hz), 8.84(1H, brs), 9.17(1H, brs), 10.76(1H, s) |
| 53 | NMR δ: 1.14(6H, d, J=12.9Hz), 2.83(1H, sep, J=12.9Hz), 2.90–3.22(6H,m), 4.38(2H, s), 4.97(1H, d, J=4.1Hz), 5.39 (2H, s), 6.20(1H, brs), 7.07–7.42(10H, m), 7.52(2H, d, J=8.8Hz), 7.67(2H, d, J=3.9Hz), 8.84(1H, brs), 9.17(1H, brs), 10.76(1H, s) |
| 54 | NMR δ: 2.95–3.02(3H, m), 3.15(3H, brs), 4.44(2H, s), 5.10(1H, dd, J=10.3, 2.5Hz), 5.58(2H, s), 6.21(1H, brs), 7.19 (2H, d, J=8.6Hz), 7.27–7.42(6H, m), 7.51(2H, d, J=8.6Hz), 7.58–7.60(1H, m), 7.69(1H, d, J=2.4Hz), 7.72(1H, d, J=2.0Hz), 7.75(1H, d, J=2.0Hz), 8.96(1H, brs), 9.44(1H, brs), 10.91(1H, s) |
| 55 | NMR δ: 2.94–3.04(3H, m), 3.15(3H, brs), 3.94(2H, s), 5.01(1H, d, J=10.3Hz), 5.31(2H, s), 6.21(1H, d, J=3.9Hz), 7.01 (1H, s), 7.17–7.41(12H, m), 7.54(2H, d, J=8.3Hz), 8.98(1H, brs), 9.35(1H, brs), 10.55(1H, s) |
| 56 | NMR δ: 2.95–3.05(3H, m), 3.15(3H, brs), 4.44(2H, s), 5.01(1H, dd, J=10.3, 2.5Hz), 5.51(2H, s), 6.20(1H, brs), 7.19 (3H, d, J=8.6Hz), 7.26–7.42(7H, m), 7.50–7.54(3H, m), 7.58(1H, d, J=2.0Hz), 7.73(1H, d, J=2.0Hz), 8.95(1H, brs), 9.43 (1H, brs), 10.98(1H, s) |
| 57 | NMR δ: 2.92–3.05(3H, m), 3.15(3H, brs), 4.43(2H, s), 5.01(1H, dd, J=10.2, 2.6Hz), 5.65(2H, s), 7.20(2H, d, J=8.4Hz), 7.29–7.48(5H, m), 7.50–7.53(3H, m), 7.70(1H, d, J=2.0Hz), 7.78(1H, d, J=2.0Hz), 7.85(1H, dt, J=8.0, 2.0Hz), 8.49 (1H, d, J=8.0Hz), 8.94(1H, brs), 9.42(1H, brs), 10.86(1H, s) |
| 58 | mp: 150–152° C., NMR δ: 2.88–3.07(3H, m), 3.08(3H, m), 3.95(2H, s), 5.00(1H, dd, J=2.8, 10.0Hz), 6.21(1H, s), 6.82(1H, d, J=7.6Hz), 6.91(1H, d, J=8.0Hz), 7.17–7.23(2H, m), 7.28–7.43(5H, m), 7.55–7.62(2H, m), 7.82–8.04(3H, m), 8.90(1H, brs), 9.31(1H, brs), 10.67(1H, brs), 14.07(1H, brs) |
| 59 | NMR δ: 2.90–3.25(6H, m), 4.95–5.04(1H, m), 5.20(1H, s), 6.22(1H, brs), 6.78(1H, s), 7.17–7.24(2H, m), 7.27–7.44 (5H, m), 7.67–7.75(2H, m), 8.50–9.10(3H, br), 9.45(1H, br), 10.22(1H, brs) |
| 60 | mp: 214–216° C., NMR δ: 2.86–3.24(6H, m), 3.65(2H, s), 4.98(1H, dd, J=2.8, 10.4Hz), 6.18(1H, d, J=6.8Hz), 6.28 (1H, d, J=8.8Hz), 7.16–7.22(2H, m), 7.28–7.45(6H,m), 7.53–7.59(2H, s), 8.85(1H, brs), 9.18(1H, brs), 10.36(1H, brs) |
| 61 | mp: 180–182° C. NMR δ: 0.87(6H, d, J=6.8Hz), 2.05–2.15(1H, m), 2.59–3.10(3H, m), 3.10–3.20(3H, m), 4.03(2H, d, J=7.8Hz), 4.41(2H, s), 5.01(1H, d, J=8.3Hz), 6.20(1H, brs), 7.21(2H, d, J=8.3Hz), 7.29–7.42(9H, m), 7.60(2H, d, J= 8.8Hz), 7.69(1H, d, J=1.9Hz), 7.75(1H, d, J=2.0Hz) |
| 62 | mp: 226–228° C., NMR δ: 2.87–3.23(6H, m), 4.45(2H, s), 5.02(1H, dd, J=2.4, 10.0Hz), 5.55(2H, s), 6.21(1H, brs), 7.16–7.46(11H, m), 7.49–7.55(2H, m), 7.66(1H, d, J=2.0Hz), 7.71(1H, d, J=2.0Hz), 8.95(1H, brs), 9.44(1H, brs), 10.93 (1H, brs), 14.82(1H, brs) |
| 63 | mp: 224–225° C., NMR δ: 2.90–3.05(3H, m), 3.05–3.25(3H, m), 4.46(2H, s), 5.01(1H, d, J=8.0Hz), 5.50(2H, s), 6.21 (1H, brs), 7.14–7.50(11H, m), 7.54(2H, d, J=8.8Hz), 7.70–7.73(2H, m), 8.93(1H, brs), 9.39(1H, brs), 10.95(1H, s) |
| 64 | mp: 205–208° C., NMR δ: 2.90–3.06(3H, m), 3.10–3.21(3H, m), 4.41(2H, s), 4.99(1H, d, J=8.3Hz), 5.51(2H, s), 6.21 (1H, s), 7.06–7.12(1H, m), 7.20(2H,d, J=8.3Hz), 7.28–7.42(6H,m), 7.69(2H, dd, J=2.0, 8.3Hz), 8.87(1H, s), 9.26(1H, s), 10.81(1H, s) |
| 65 | mp: 211–216° C., NMR δ: 3.00(3H, brs), 3.15(3H, brs), 4.44(2H, s), 5.05(1H, dd, J=10.2, 1.9Hz), 5.58(2H, s), 6.22 (1H, brs), 7.14–7.22(1H, m), 7.29–7.32(1H, m), 7.37–7.42(4H, m), 7.47–7.54(3H, m), 7.65(1H, s), 7.69(1H, d, J=1.9Hz), 9.02(1H, brs), 9.55(1H, brs), 10.97(1H, s) |
| 66 | mp: 199–201° C., NMR δ: 2.87–3.23(6H, m), 4.45(2H, s), 4.95–5.04(1H, m), 5.51(2H, s), 6.20(1H, brs), 7.10–7.43 (10H, m), 7.49–7.55(2H, m), 7.71(1H, d, J=2.0Hz), 7.74(1H, d, J=2.0Hz), 8.89(1H, brs), 9.30(1H, brs), 10.90(1H, brs), 14.73(1H, brs) |
| 67 | mp: 131–135° C., NMR δ: 3.00(3H, brs), 3.16(3H, brs), 4.49(2H, s), 5.04(1H, d, J=10.0Hz), 5.56(2H, s), 6.23(1H, brs), 7.20(2H, d, J=8.2Hz), 7.23–7.34(4H, m), 7.37–7.42(4H,m), 7.53(2H, d, J=8.2Hz), 7.72(2H, s), 9.01(1H, brs), 9.54 (1H, brs), 11.00(1H, s) |
| 68 | mp: 217–219° C., NMR δ: 2.90–3.05(3H, m), 3.05–3.20(3H, m), 4.46(2H, s), 5.00(1H, d, J=8.0Hz), 5.47(2H, s), 6.21 (1H, brs), 7.20(2H, d, J=8.0Hz), 7.25–7.50(7H, m), 7.50–7.60(3H, m), 7.70(1H, d, J=1.9Hz), 7.71(1H, d, J=2.0Hz), 8.91(1H, brs), 9.33(1H, brs), 10.93(1H, s) |
| 69 | mp: 213–217° C., NMR δ: 2.90–3.05(3H,m), 3.05–3.20(3H,m), 4.42(2H, s), 5.02(1H, dd, J=10.2, 2.4Hz), 5.62(2H, s), 6.21(1H, brs), 7.20(2H, d, J=8.3Hz), 7.29–7.42(6H, m), 7.49(2H, d, J=8.3Hz), 7.51–7.60(1H, m), 7.68–7.73(2H, m), 8.95(1H, brs), 9.42(1H, brs), 10.89(1H, s) |
| 70 | mp: 212–213° C., NMR δ: 2.87–3.23(6H, m), 4.47(2H, s), 5.02(1H, dd, J=2.4, 10.0Hz), 5.53(2H, s), 6.21(1H, brs), |

TABLE 2-continued

| Ex. | DATA |
|---|---|
| | 7.16–7.23(2H, m), 7.28–7.34(1H, m), 7.36–7.43(4H, m), 7.48–7.55(2H, m), 7.57–7.67(2H, m), 7.69–7.74(2H, m), 8.95 (1H, brs), 9.43(1H, brs), 10.95(1H, brs), 14.86(1H, brs) |
| 71 | mp: 209–213° C., NMR δ: 2.90–3.05(3H, m), 3.05–3.20(3H, m), 4.47(2H, s), 4.98–5.01(1H, m), 5.49(2H, s), 6.21 (1H, brs), 7.21(2H, d, J=8.3Hz), 7.28–7.34(1H, m), 7.36–7.44(6H,m), 7.53(2H, d, J=8.8Hz), 7.71(1H, d, J=1.9Hz), 7.74 (1H, d, J=1.9Hz), 8.91(1H, brs), 9.34(1H, brs), 10.97(1H, s) |
| 72 | mp: 190–193° C., NMR δ: 2.90–3.08(3H, m), 3.10–3.21(3H,m ), 4.38(2H, s), 4.99(1H, dd, J=2.5, 10.2Hz), 5.69(2H, s), 6.20(1H, s), 7.21(2H, d, J=8.8Hz), 7.29–7.42(5H, m), 7.48(2H, d, J=8.3Hz), 7.70(1H, d, J=1.9Hz), 7.77(1H, s), 8.88 (1H, s), 9.27(1H, s), 10.84(1H, s) |
| 73 | mp: 233–234° C., NMR δ: 2.90–3.23(6H, m), 4.47(2H, s), 5.02(1H, dd, J=2.4, 10.0Hz), 5.44(2H, s), 6.21(1H, brs), 7.12–7.23(3H, m), 7.28–7.34(1H, m), 7.36–7.44(5H, m), 7.52–7.58(2H, m), 7.66–7.73(3H, m), 7.79–7.81(1H, m), 8.96 (1H, brs), 9.44(1H, brs), 10.96(1H, brs), 14.79(1H, brs) |
| 74 | mp: 180–183° C., NMR δ: 2.67–2.76(4H, m), 2.78–2.86(2H, m), 4.00(2H, s), 4.66(1H, dd, J=8.3, 3.9Hz), 5.39(2H, s), 5.42(1H, d, J=0.9Hz), 6.57(1H, d, J=0.9Hz), 6.78(1H, brs), 7.03(2H, d, J=8.3Hz), 7.21–7.26(1H, m), 7.27–7.34(4H, m), 7.46–7.50(1H, m), 7.52(2H, d, J=8.3Hz), 7.56(1H, s), 7.58(1H, s), 8.32(1H, s), 10.32(1H, s) |
| 75 | mp: 210–215° C., NMR δ: 2.91–3.03(3H, m), 3.15(3H, brs), 4.44(2H, s), 5.01(1H, dd, J=10.4, 2.6Hz), 5.53(2H, s), 6.21(1H, brs), 7.18(2H, d, J=8.3Hz), 7.30–7.32(1H, m), 7.37–7.42(4H, m), 7.48(2H, d, J=7.49(2H, d, J=8.3Hz), 7.74(1H, d, J=2.0Hz), 7.75(1H, d, J=2.0Hz), 7.79(2H, d, J=8.3Hz), 8.94(1H, brs), 9.39(1H, brs), 10.93(1H, s) |
| 76 | mp: 162–165° C., NMR δ: 2.93–3.05(3H, m), 3.14(3H, brs), 4.47(2H, s), 5.03(1H, dd, J=10.3, 2.5Hz), 5.62(1H, brs), 5.89(2H, s), 7.12(2H, d, J=8.3Hz), 7.30–7.37(1H, m), 7.39–7.43(6H,m), 7.61(2H, d, J=8.8Hz), 7.69(1H, t, J=7.5Hz), 7.75(1H, d, J=1.9Hz), 7.83–7.86(2H, m), 7.97(1H, d, J=8.3Hz), 8.44(1H, d, J=8.3Hz), 8.99(1H, brs), 9.52(1H, brs), 10.84 (1H, s) |
| 77 | NMR δ: 2.64–2.74(4H, m), 2.77–2.82(2H, m), 3.93(2H, s), 4.63(1H, dd, J=7.8, 4.Hz), 5.33(2H, s), 6.80(2H, d, J=6.3 Hz), 7.14(2H, d, J=8.8Hz), 7.20–7.24(1H, m), 7.28–7.35(5H, m), 7.43(1H, d, J=7.8Hz), 7.47–7.52(3H, m), 10.27(1H, s) |
| 78 | NMR δ: 2.63–2.72(4H, m), 2.75–2.81(2H, m), 3.79(2H, s), 4.62(1H, dd, J=7.8, 4.4Hz), 5.30(1H, brs), 5.33(2H, s), 6.68 (1H, d, J=1.0Hz), 6.91(1H, dd, J=8.8, 5.9Hz), 7.06(1H, d, J=1.0Hz), 7.12(2H, d, J=8.8Hz), 7.19–7.24(2H, m), 7.28–7.33(4H, m), 7.43(2H, d, J=8.3Hz), 7.49(1H, dd, J=8.3, 2.5Hz), 8.32(1H, s), 10.21(1H, s) |
| 79 | NMR δ: 2.88–3.08(3H, m), 3.10–3.22(3H, m), 4.40(2H, s), 4.97(1H, d, J=8.3Hz), 5.56(2H, s), 6.20(1H, s), 7.19(2H, d, J=8.3Hz), 7.24(1H, d, J=2.5Hz), 7.30–7.60(9H, m), 7.64(1H, d, J=2.0Hz), 7.72(1H, s), 8.83(1H, s), 9.14(1H, s), 10.71 (1H, s) |
| 80 | NMR δ: 2.90–3.08(3H, m), 3.10–3.22(3H, m), 4.44(2H, s), 5.02(1H, d, J=8.8Hz), 5.59(2H, s), 6.21(1H, s), 7.20(2H, d, J=8.0Hz), 7.24–7.42(7H, m), 7.50(2H, d, J=8.8Hz), 7.72(2H, d, J=6.8Hz), 8.94(1H, s), 9.42(1H, s), 10.93(1H, s) |
| 81 | NMR δ: 2.87–3.23(6H,m), 3.85(3H, s), 4.30(2H, s), 4.94–5.01(1H, m), 5.55(2H, s), 6.17–6.22(1H, br), 7.14–7.23(2H, m), 7.28–7.50(9H, m), 7.57–7.64(2H, m), 7.87–7.93(2H, m), 8.83(1H, brs), 9.10(1H, brs), 10.68(1H, brs), 14.86(1H, brs) |
| 82 | NMR δ: 1.30–1.64(6H, m), 2.88–3.22(8H,m), 3.45–3.65(2H, m), 4.39(2H, s), 4.97(1H, d, J=9.8Hz), 5.50(2H, s), 6.21 (1H, s), 7.20(2H, d, J=8.3Hz), 7.30–7.42(9H, m), 7.51(2H, d, J=8.7Hz), 7.71(2H, d, J=7.8Hz), 8.81(1H, s), 9.14(1H, s), 10.77(1H, s) |
| 83 | mp: 229–232° C., NMR δ: 2.90–3.00(3H, m), 3.10–3.18(3H, m), 5.00(1H, dd, J=2.8, 10.1Hz), 5.03(2H, s), 6.27(1H, t, J=2.0Hz), 7.20(2H, d, J=8.8Hz), 7.29–7.42(5H, m), 7.46(1H, d, J=2.4Hz), 7.58(2H, d, J=8.8Hz), 7.77(1H, d, J=2.0Hz), 8.91(1H, s), 9.32(1H, s), 10.53(1H, s) |
| 84 | mp: 237–240° C., NMR δ: 2.90–3.08(3H, m), 3.10–3.22(3H, m), 4.96(1H, dd, J=2.0, 10.0Hz), 5.15(2H, s), 7.21(2H, d, J=8.0Hz), 7.28–7.42(5H, m), 7.56(2H, d, J=8.4Hz), 8.03(1H, s), 8.61(1H, s), 8.82(1H,s), 9.09(1H, s), 10.57(1H, s) |
| 85 | mp: 244–248° C., NMR δ: 2.90–3.06(3H, m), 3.10–3.20(3H, m), 5.00(1H, d, J=7.6Hz), 5.20(2H, s), 6.20(1H, s), 7.20–7.50(11H, m), 7.59(2H, d, J=7.2Hz), 8.94(3H, s), 9.36(1H, s), 10.95(1H, s), 12.92(1H, s) |
| 86 | mp: 223–224° C., NMR δ: 2.86–3.22(6H, m), 3.49(2H, s), 4.93–5.03(1H, m), 6.20(1H, d, J=4.0Hz), 7.15–7.43(9H, m), 7.55–7.62(2H, m), 7.75(1H, dt, J=1.6, 8.0Hz), 8.45–8.53(1H, m), 8.06–9.50(2H, br), 10.35(1H, brs) |
| 87 | mp: 236–238° C., NMR δ: 2.86–3.23(6H, m), 3.72(2H, s), 4.91–5.02(1H, m), 6.20(1H, d, J=4.0Hz), 7.15–7.22(2H, m), 7.27–7.45(6H, m), 7.53–7.62(2H, m), 7.73–7.82(1H, m), 8.40–8.60(2H, m), 8.84(1H, brs), 9.16(1H, brs), 10.35–10.50 (1H, br) |
| 88 | mp: 195–198° C., NMR δ: 2.86–3.22(6H, m), 3.73(2H, s), 4.93–5.04(1H, m), 6.15–6.25(1H, br), 7.14–7.22(2H, m), 7.28–7.43(7H, m), 7.54–7.63(2H, m), 8.47–8.53(2H, m), 9.07(2H, brs), 10.50(1H, brs) |
| 89 | mp: 202–204° C., NMR δ: 2.71–2.81(2H, m), 2.88–3.24(8H, m), 3.49(2H, s), 4.93–5.05(1H, m), 6.20(1H, brd, J=3.2 Hz), 7.15–7.23(3H, m), 7.26–7.44(6H, m), 7.52–7.60(2H m), 7.69(1H, dt, J=1.6, 7.6Hz), 8.45–8.51(1H, m), 9.07(2H, brs), 10.07(1H, brs) |
| 90 | mp: 220–227° C., NMR δ: 2.80–3.20(8H, m), 4.31(2H, s), 4.42(2H, t, J=8.0Hz), 5.00(1H, d, J=1.0Hz), 6.21(1H, brs), 7.20–7.40(12H, m), 7.59(2H, d, J=8.6Hz), 7.65(2H, dd, J=12.9, 0.9Hz), 8.91(1H, brs), 9.34(1H, brs), 10.98(1H, s) |
| 91 | mp: 158–165° C., NMR δ: 2.51–2.78(6H, m), 3.96(2H, s), 4.59(1H, t, J=5.2Hz), 5.20(1H, brs), 7.13–7.32(9H, m), 7.50–7.53(4H, m), 10.33(1H, brs), 12.37(1H, brs) |
| 92 | mp: 216–217° C., NMR δ: 2.31(3H, s), 2.86–3.24(6H, m), 3.89(2H, s), 4.92–5.07(1H, m), 6.20(1H,d, J=4.0Hz), 7.12–7.22(3H, m), 7.28–7.45(5H, m), 7.50–7.64(2H, m), 8.30(1H, d, J=4.4Hz), 8.60–9.50(2H, br), 10.32(1H, brs) |
| 93 | mp: 236–238° C., NMR δ: 2.86–3.24(6H, m), 3.95(2H, s), 4.91–5.01(1H, m), 5.44(2H, s), 6.19(1H, d, J=4.0Hz), 7.15–7.22(2H, m), 7.27–7.43(5H, m), 7.52–7.62(2H, m), 8.83(1H, br), 9.12(1H, brs), 10.41(1H, brs) |
| 94 | NMR δ: 2.90–3.10(3H, m), 3.10–3.20(3H, m), 4.38(2H, s), 4.98(1H, t, J=10.4Hz), 5.44(2H, s), 6.20(1H, d, J=3.2Hz), 7.20(2H, d, J=8.4Hz), 7.30–7.45(9H, m), 7.53(2H, d, J=8.8Hz), 7.64(2H, s), 8.85(1H, brs), 9.21(1H, brs), 10.79(1H, s) |
| 95 | NMR δ: 2.31(3H, s), 2.89–3.17(6H, m), 3.79(2H, s), 4.98(1H, dt, J=3.2, 10.4Hz), 7.10–7.41(12H, m), 10.32(1H, s) |
| 96 | NMR δ: 2.27(3H, s), 2.89–3.17(6H, m), 3.79(2H, s), 4.99(1H, dt, J=3.6, 10.0Hz), 7.17–7.59(12H, m), 10.31(1H, s) |
| 97 | NMR δ: 2.44(3H, s), 2.78–3.20(6H, m), 3.80(2H, s), 4.97(1H, dt, J=3.2, 10.4Hz), 7.12–7.66(12H, m), 10.33(1H, s) |
| 98 | NMR δ: 1.06(3H, d, J=6.4Hz), 2.50–2.65(2H, m), 2.90–3.15(3H, m), 3.83(2H, s), 4.80–4.94(1H, m), 7.10–7.18(2H, m), 7.23–7.45(7H, m), 7.52–7.60(2H, m), 7.71–7.80(1H, m), 8.41–8.52(1H, m), 10.25(1H, brs) |
| 99 | mp: 203–204° C., NMR δ: 1.13(3H, d, J=6.4Hz), 2.55–2.64(1H, m), 3.00–3.50(4H, m), 3.84(2H, s), 4.92–5.02(1H, m), 6.20(1H, d, J=4.0Hz), 7.13–7.20(2H, m), 7.24–7.46(7H, m), 7.54–7.60(2H, m), 7.73–7.80(1H, m), 8.51(1H, brs), 8.67 (1H, brs), 9.13(1H, brs), 10.31(1H, brs) |
| 100 | NMR δ: 1.06(3H, d, J=6.4Hz), 2.50–2.65(1H, m), 2.57–3.50(4H, m), 3.78(2H, s), 4.77–4.92(1H, m), 5.25(2H, s), 6.85 (1H, s), 7.10–7.55(15H, m), 10.33(1H, brs) |
| 101 | mp: 194–196° C., NMR δ: 2.88–3.25(6H, m), 3.89(2H, s), 5.20–5.26(1H, m), 6.30(1H, s), 7.17–7.48(7H, m), 7.54–7.60(3H, m), 7.81–7.88(1H, m), 8.54(1H, d, J=4.0Hz), 8.82(1H, s), 9.16(1H, s), 10.35(1H, s) |

TABLE 2-continued

| Ex. | DATA |
|---|---|
| 102 | mp: 214–215° C., NMR δ: 2.88–3.25(6H, m), 3.85(2H, s), 4.96–5.02(1H, m), 6.33(1H, d, J=3.8Hz), 7.12–7.31(6H, m), 7.39–7.48(2H, m), 7.58(2H, d, J=8.3Hz), 7.74–7.80(1H, m), 8.50(1H, s), 8.82(1H, s), 9.01(1H, s), 10.30(1H, s) |
| 103 | mp: 223–225° C., NMR δ: 2.88–3.06(3H, m), 3.10–3.20(3H, m), 3.84(2H, s), 4.94–5.01(1H, m), 6.24(1H, d, J=4.0Hz), 7.16–7.30(5H, m), 7.38–7.46(3H, m), 7.58(2H, d, J=8.8Hz), 7.76(1H, dt, J=1.6, 7.6Hz), 8.50(1H, d, J=8.8Hz), 8.83 (1H, s), 9.08(1H, s), 10.31(1H, s) |
| 104 | mp: 208–210° C., NMR δ: 2.88–3.24(6H, m), 3.99(2H, s), 4.90–5.10(1H, m), 6.20(1H, d, J=3.6Hz), 7.15–7.24(2H, m), 7.28–7.44(6H, m), 7.53–7.62(2H, m), 8.50–9.30(4H, m), 10.33(1H, brs) |
| 105 | mp: 234–235° C., NMR δ: 2.94–3.25(6H, m), 4.07(2H, s), 4.90–5.02(1H, m), 6.20(1H, d, J=4.0Hz), 7.16–7.23(2H, m), 7.27–7.44(5H,m), 7.53–7.65(4H, m), 7.71–7.78(1H, m), 7.94–8.00(2H, m), 8.33(1H, d, J=8.0Hz), 8.50–9.25(2H, m), 10.46(1H, brs) |
| 106 | mp: 221–222° C., NMR δ: 2.90–3.25(6H, m), 3.85(2H, s), 4.92–5.08(1H, m), 6.35(1H, d, J=3.6Hz), 7.14–7.23(2H, m), 7.23–7.31(1H, m), 7.33–7.50(5H, m), 7.54–7.64(2H, m), 7.76(1H, dt, J=1.6, 7.6Hz), 8.43–8.55(1H, m), 8.80–9.40 (2H, br), 10.36(1H, brs) |
| 107 | mp: 204–205°0 C., NMR δ: 2.85–3.28(6H, m), 3.85(2H, s), 5.02–5.14(1H, m), 6.37(1H, d, J=4.0Hz), 7.14–7.32(3H, m), 7.365–7.46(2H, m), 7.55–7.64(2H, m), 7.70–7.86(2H, m), 8.46–8.56(2H, m), 8.57–8.65(1H, m), 9.13(2H, brs), 10.37 (1H, brs) |
| 108 | NMR δ: 2.63–2.67(4H, m), 2.73–2.78(2H, m), 4.07(2H, s), 4.60(1H, dd, J=7.4, 4.9Hz), 5.24(1H, brs), 5.57(2H, s), 7.12–7.23(7H, m), 7.27–7.31(4H, m), 7.37(3H, d, J=8.3Hz), 7.46(2H, d, J=8.3Hz), 7.60–7.61(1H, m), 8.31(1H, s), 10.31 (1H, s) |
| 109 | NMR δ: 2.26(3H, s), 2.40(3H, s), 2.90–3.17(6H, m), 3.75(2H, s), 4.99(1H, dt, J=3.2, 6.8Hz), 6.97–7.60(11H, m), 10.35 (1H, s) |
| 110 | mp: 183–184° C., NMR δ: 1.85–2.05(2H, m), 2.53–2.65(2H, m), 2.83–3.03(3H, m), 3.05–316(1H, m), 3.88(2H, s), 4.95(1H, d, J=9.6Hz), 6.15(1H, brs), 7.10–7.18(2H, m), 7.22–7.43(7H, m), 7.50–7.60(2H, m), 7.75(1H, dt, J=1.6, 7.2Hz), 8.45–8.53(1H, m), 8.91(2H, brs), 10.29(1H, brs) |
| 111 | mp: 225–226° C., NMR δ: 3.02–3.14(1H, m), 3.18–3.46(3H, m), 3.84(2H, s), 4.22–4.35(2H, m), 4.98–5.08(1H, m), 6.21(1H, d, J=3.6Hz), 6.90–6.97(2H, m), 7.23–7.44(7H, m), 7.53–7.62(2H, m), 7.76(1H, dt, J=1.6, 7.2Hz), 8.45–8.54 (1H, m), 8.80–9.50(2H, br), 10.29(1H, brs) |
| 112 | NMR δ: 1.21(6H, s), 2.85–3.23(4H, m), 3.89(2H, s), 4.90–5.00(1H, m), 6.21(1H, brs), 7.11–7.19(2H, m), 7.28–7.50 (7H, m), 7.53–7.62(2H, m), 7.78–7.90(1H, m), 8.45–8.60(2H, m), 9.00–9.10(1H, br), 10.35(1H, brs) |
| 113 | mp: 132–133° C., NMR δ: 2.90–3.10(3H, m), 3.13–3.23(3H, m), 4.96(1H, dd, J=2.5, 10.2Hz), 7.06–7.11(1H, m), 7.21(2H, d, J=8.7Hz), 7.30–7.42(5H, m), 7.47–7.53(3H, m), 7.81–7.87(1H, m), 8.29(1H, d, J=4.9Hz), 8.78(1H, s), 9.00 (1H, s), 9.88(1H, s), 10.51(1H, s) |

TABLE 3

| Ex. | Structure |
|---|---|
| 1 | 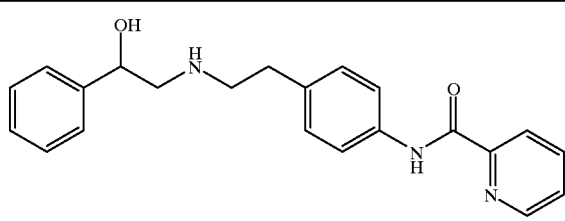 |
| 23 | 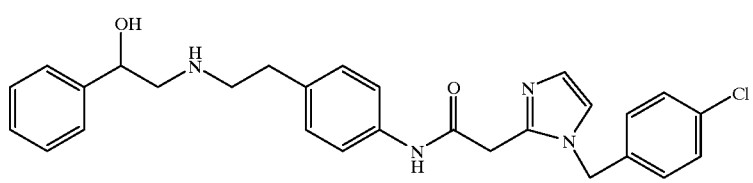 |
| 33 | 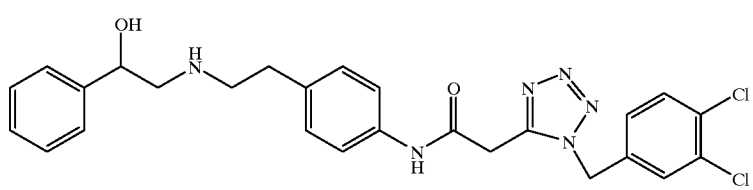 |

TABLE 3-continued

| Ex. | Structure |
|---|---|
| 41 | 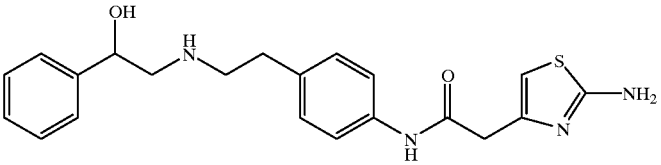 |
| 47 | 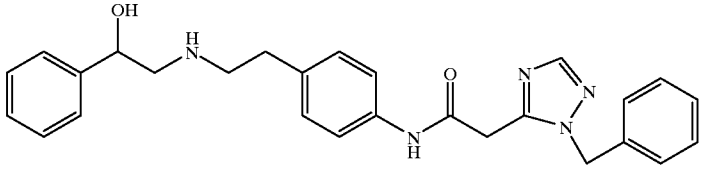 |
| 58 | 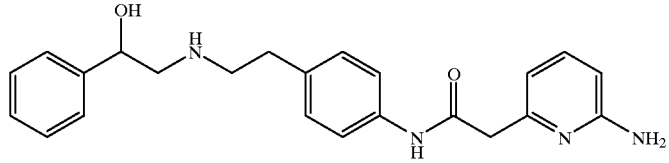 |
| 86 | 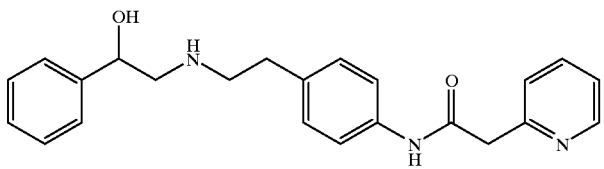 |
| 93 | 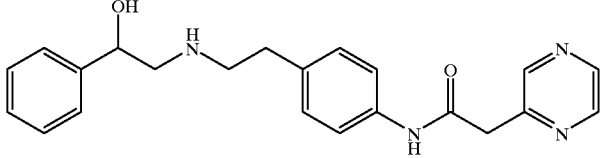 |
| 104 | 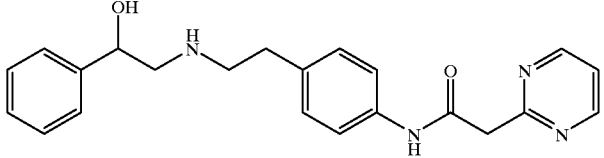 |

The compounds shown in Tables 4 and 5 together with chemical structural formulae can be easily manufactured by almost the same method as mentioned in the above Examples or Manufacturing Methods or by the method to which some modifications known to the persons skilled in the art are applied. Incidentally, in some cases, there are tautomeric, geometric or optical isomers for the compounds mentioned in Tables 4 and 5, and the compounds of the present invention cover each of the isolated isomers of the above-mentioned ones or a mixture thereof.

TABLE 4
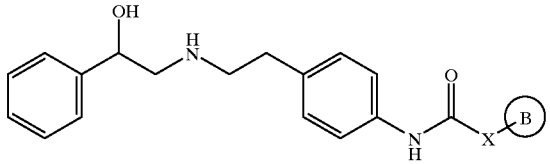
| No. | |
|---|---|
| 1 | 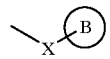 |
| 2 | 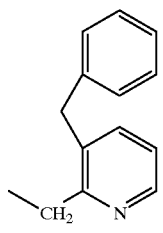 |
| 3 | 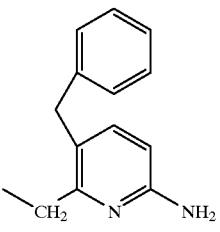 |
| 4 | 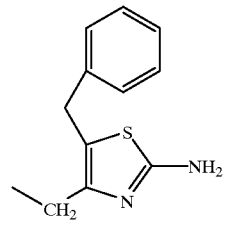 |
| 5 | 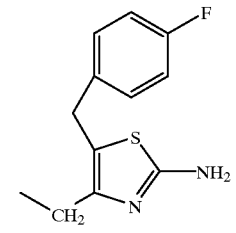 |
TABLE 4-continued
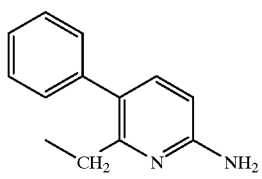
| No. | |
|---|---|
| 6 | 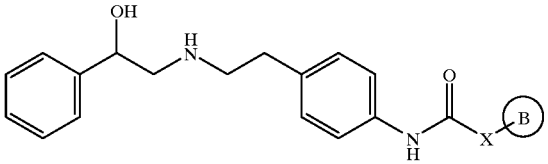 |
| 7 | 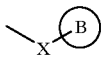 |
| 8 | 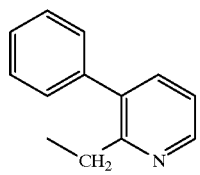 |
| 9 | 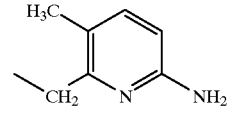 |
| 10 | 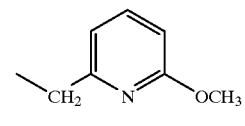 |
| 11 | 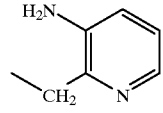 |
| 12 | 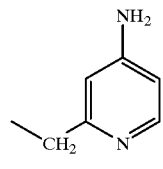 |

TABLE 5

General structure:

Structure with R²ᵃ-phenyl-CH(OH)-CH₂-NH-CH₂CH₂-(4-phenyl)-NH-C(=O)-X-B

| No. | R²ᵃ | X–B |
|-----|-----|-----|
| 13 | H | -CH₂-(1,2,4-triazol-1-yl)-N-CH₂-(4-fluorophenyl) |
| 14 | H | -CH₂-(4,5-dimethylimidazol-2-yl)-N-CH₂-(4-fluorophenyl) |
| 15 | H | -CH₂-(5-ethylimidazol-2-yl)-N-CH₂-(4-fluorophenyl) |
| 16 | H | -CH₂-(5-aminoimidazol-2-yl)-N-CH₂-(4-fluorophenyl) |
| 17 | H | -CH₂-(tetrazol-5-yl)-N-CH₂-(4-fluorophenyl) |
| 18 | H | -CH₂-(5-chloroimidazol-2-yl)-N-CH₂-(4-fluorophenyl) |
| 19 | H | -CH₂-(5-hydroxymethylimidazol-2-yl)-N-CH₂-(4-fluorophenyl) |
| 20 | H | -CH₂-(4-aminoimidazol-2-yl)-N-CH₂-(4-fluorophenyl) |
| 21 | Cl | -CH₂-(2-aminothiazol-4-yl) |
| 22 | Cl | -CH₂-(imidazol-2-yl)-N-CH₂-(4-chlorophenyl) |

What is claimed is:

1. A compound of formula (I):

(I)

[Structure of formula (I): R²-phenyl(Z)-CH(OH)-CH₂-NH-C(R¹ᵃ)(R¹ᵇ)-A-phenyl-NH-C(=O)-X-B]

in the formula, each of the symbols means as follows:
  ring B is a heteroaryl group which is unsubstituted or substituted and is optionally fused with a benzene ring;
  X is a bond, or a lower alkylene or an alkenylene, both of which are unsubstituted or substituted with hydroxy or a lower alkyl group, or X is a carbonyl or a group represented by —NH—, and when X is a lower alkylene which is substituted with a lower alkyl group, a carbon atom of the ring B optionally bonds with the lower alkyl group so that a ring is formed;
  A is a lower alkylene or a group represented by -lower alkylene-O—;
  $R^{1a}$, $R^{1b}$ are the same or different and each is a hydrogen atom or a lower alkyl group;
  $R^2$ is a hydrogen atom or a halogen atom; and
  Z is a group represented by =CH—; or a salt thereof.

2. The compound of formula (I) or the salt thereof according to claim 1, wherein A is methylene, ethylene, or a group represented by —CH₂O—.

3. The compound of formula (I) or the salt thereof according to claim 2, wherein the ring B is a heteroaryl group which is substituted with a substituent chosen from a halogen atom, lower alkyl, lower alkenyl, lower alkynyl, hydroxy, sulfanyl, halogeno lower alkyl, lower alkyl-O—, lower alkyl-S—, lower alkyl-O—CO—, carboxy, sulfonyl, sulfinyl, lower alkyl-SO—, lower alkyl-SO$_2$—, lower alkyl-CO—, lower alkyl-CO—O—, carbamoyl, lower alkyl-NH—CO—, di-lower alkyl-N—CO—, nitro, cyano, amino, lower alkyl-NH—, di-lower alkyl-N—, aryl-lower alkyl, halogeno aryl-lower alkyl, guanidino, lower alkyl-CO—NH, and lower alkyl-SO$_2$—NH—.

4. The compound of formula (I) or the salt thereof according to claim 3, wherein R$^2$, R$^{1a}$ and R$^{1b}$ are each a hydrogen atom, and Z is =CH—.

5. A compound of formula (Ia):

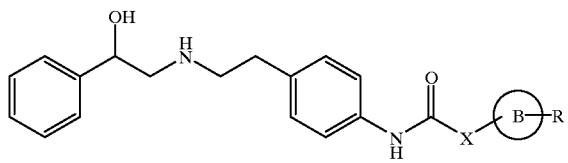

(Ia)

in the formula, each of the symbols means as follows:
ring B is a heteroaryl group;
X is a bond or a lower alkylene group;
R is a hydrogen atom, a halogen atom, a lower alkyl group, amino group, an aryl lower alkyl group, or a halogeno aryl-lower alkyl group; or a salt thereof.

6. A compound:
(R)-4'-[2-[(2-Hydroxy-2-phenylethyl)amino]ethyl]-2-pyridinecarboxyanilide,
(R)-2-[1-(4-chlorobenzyl)-1H-imidazol-2-yl]-4'-[2-[(2-hydroxy-2-phenylethyl)amino]ethyl]-acetanilide, (R)-2-[1-(3,4-dichlorobenzyl)-1H-tetrazol-5-yl]-4'-[2-[(2-hydroxy-2-phenylethyl)amino]ethyl]acetanilide,
(R)-2-(2-aminothiazol-4-yl)-4'-[2-(2-hydroxy-2-phenylethyl)amino]ethyl]acetanilide,
(R)-2-(2-benzyl-1H-1,2,4-triazol-3-yl)-4'-[2-[(2-hydroxy-2-phenylethyl)-amino]ethyl]acetanilide,
(R)-2-(2-aminopyridin-6-yl)-4'-[2-[(2-hydroxy-2-phenylethyl)amino]ethyl]acetanilide, (R)-4'-[2-[(2-hydroxy-2-phenylethyl)amino]ethyl]-2-(2-pyridyl)acetanilide,
(R)-4'-[2-[(2-hydroxy-2-phenylethyl)-amino]ethyl)-2-(2-pyrazinyl)acetanilide, (R)-4'-[2-[(2-hydroxy-2-phenylethyl)amino]ethyl)-2-(2-pyrimidinyl)-acetanilide, or a salt of any of the foregoing.

7. A composition comprising at least one compound of formula (I) or the salt thereof as claimed in one of claims 1 through 4 in a pharmaceutically acceptable carrier.

8. The composition as claimed in claim 7, wherein the at least one compound of formula (I) or the salt thereof is present in an amount effective for the treating of diabetes mellitus in a human or animal patient in need of such treating.

9. The compound of formula (I) as claimed in claim 1, wherein the compound of formula (I) is an optical isomer, a hydrate, or a solvate of the compound of formula (I).

10. A composition comprising a compound of formula (I) as claimed in claim 1 in a pharmaceutically acceptable carrier, wherein the compound of formula (I) is present as a polymorphic substance.

11. A composition comprising at least one compound of formula (I) or the salt thereof as claimed in claim 5, in a pharmaceutically acceptable carrier.

12. A composition comprising at least one compound or the salt of any of the foregoing as claimed in claim 6, in a pharmaceutically acceptable carrier.

13. A method for treating diabetes mellitus in a human or animal patient in need of such treatment comprising administering to the patient an amount of a compound of formula (I) as claimed in claim 1, wherein the amount is an amount effective for such treatment.

14. A method for treating obesity in a human or animal patient in need of such treatment comprising administering to the patient an amount of a compound of formula (I) as claimed in claim 1, wherein the amount is an amount effective for such treatment.

* * * * *

UNITED STATES PATENT AND TRADEMARK OFFICE
CERTIFICATE OF CORRECTION

PATENT NO. : 6,346,532 B1
DATED : February 12, 2002
INVENTOR(S) : T. Maruyama et al.

It is certified that error appears in the above-identified patent and that said Letters Patent is hereby corrected as shown below:

Column 16,
Lines 29-30, (Example 3) should read: -- (R)-4'-[2-[(2-Hydroxy-2-phenylethyl)amino]ethyl]-8-quinolinecarboxanilide dihydrochloride Column 17,
Lines 40-41, (Example 16) should read:
-- (R)-2-(2-Benzyloxypyridin-6-yl)-4'-[2-[(2-hydroxy-2-phenylethyl)amino]ethyl] acetanilide hydrochloride --

Column 19,
Lines 58-60, (Example 39) should read: -- (R)-4'-[2-[(2-Hydroxy-2-phenylethyl)amino]ethyl]-2-(2-phenylaminothiazol-4-yl)acetanilide hydrochloride --

Column 23,
Lines 3-5, (Example 66) should read:
-- (R)-2-[ 1-(3,5-Difluorobenzyl)-1H-imidazol-2-yl]-4'-[2-(2-hydroxy-2-phenylethyl)amino]ethyl] acetanilide dihydrochloride --

Column 26,
Lines 47-49, (Example 99) should read: -- 4'[(S)-2-[((R)-2-Hydroxy-2-phenylethyl)amino]propyl]-2-(2-pyridyl)acetanilide hydrochloride --

UNITED STATES PATENT AND TRADEMARK OFFICE
CERTIFICATE OF CORRECTION

PATENT NO.    : 6,346,532 B1
DATED         : February 12, 2002
INVENTOR(S)   : T. Maruyama et al.

It is certified that error appears in the above-identified patent and that said Letters Patent is hereby corrected as shown below:

Column 28,
Line 2, change "30/1 Δ 10/1)." to -- 30/1 → 10/1). --.
Line 7, should read: -- [(2-hydroxy-2-phenylethyl)amino]propyl]-2-(2-pyridyl) --
Lines 62-63, (Example 113) should read: -- (R)-1-[4-[2-[(2-Hydroxy-2-phenylethyl)amino]ethyl] phenyl]-3-(2-pyridyl)urea dihydrochloride --

Column 45,
Line 4, should read: -- (R)-2-[1-(4-chlorobenzyl)-1H-imidazol-2-yl]-4'-[2-[(2- --

Signed and Sealed this

Thirtieth Day of July, 2002

Attest:

JAMES E. ROGAN
Attesting Officer          Director of the United States Patent and Trademark Office

(12) EX PARTE REEXAMINATION CERTIFICATE (25th)
Ex Parte Reexamination Ordered under 35 U.S.C. 257

United States Patent
Maruyama et al.

(10) Number: US 6,346,532 C1
(45) Certificate Issued: Feb. 24, 2015

(54) AMIDE DERIVATIVES OR SALTS THEREOF

(75) Inventors: Tatsuya Maruyama, Tsukuba (JP); Takayuki Suzuki, Tsukuba (JP); Kenichi Onda, Tsukuba (JP); Masahiko Hayakawa, Tsukuba (JP); Hiroyuki Moritomo, Tsukuba (JP); Tetsuya Kimizuka, Tsukuba (JP); Tetsuo Matsui, Tsukuba (JP)

(73) Assignee: Astellas Pharma Inc., Chuo-Ku, Tokyo (JP)

Supplemental Examination Request:
No. 96/000,045, Nov. 21, 2013

Reexamination Certificate for:
Patent No.: 6,346,532
Issued: Feb. 12, 2002
Appl. No.: 09/529,096
PCT Filed: Oct. 15, 1998
PCT No.: PCT/JP98/04671
§ 371 (c)(1),
(2), (4) Date: Apr. 7, 2000
PCT Pub. No.: WO99/20607
PCT Pub. Date: Apr. 29, 1999

Certificate of Correction issued Jul. 13, 2002

(51) Int. Cl.
| | |
|---|---|
| A61K 31/495 | (2006.01) |
| A61K 31/505 | (2006.01) |
| C07D 239/02 | (2006.01) |
| C07D 213/00 | (2006.01) |
| C07D 249/00 | (2006.01) |
| C07D 215/48 | (2006.01) |
| C07D 277/82 | (2006.01) |
| C07D 233/26 | (2006.01) |
| C07D 235/30 | (2006.01) |
| C07D 213/81 | (2006.01) |
| C07D 401/04 | (2006.01) |
| C07D 241/12 | (2006.01) |
| C07D 277/36 | (2006.01) |
| C07D 513/04 | (2006.01) |
| C07D 231/12 | (2006.01) |
| C07D 213/30 | (2006.01) |
| C07D 257/04 | (2006.01) |
| C07D 239/26 | (2006.01) |
| C07D 213/56 | (2006.01) |

(52) U.S. Cl.
CPC ............ *C07D 213/30* (2013.01); *C07D 215/48* (2013.01); *C07D 277/82* (2013.01); *C07D 233/26* (2013.01); *C07D 235/30* (2013.01); *C07D 213/81* (2013.01); *C07D 401/04* (2013.01); *C07D 241/12* (2013.01); *C07D 277/36* (2013.01); *C07D 513/04* (2013.01); *C07D 231/12* (2013.01); *C07D 257/04* (2013.01); *C07D 239/26* (2013.01); *C07D 213/56* (2013.01)
USPC ........ 514/252.1; 514/256; 544/330; 544/332; 546/1; 546/152; 548/186; 548/190; 548/214; 548/252; 548/260

(58) Field of Classification Search
None
See application file for complete search history.

(56) References Cited

To view the complete listing of prior art documents cited during the supplemental examination proceeding and the resulting reexamination proceeding for Control Number 96/000,045, please refer to the USPTO's public Patent Application Information Retrieval (PAIR) system under the Display References tab.

*Primary Examiner* — Evelyn Huang

(57) ABSTRACT

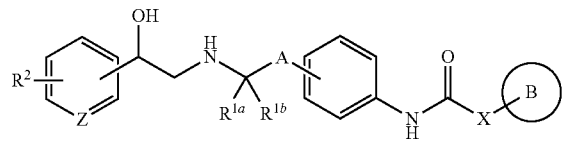

Amide derivatives represented by general formula (I) or salts thereof wherein each symbol has the following meaning: ring B: an optionally substituted heteroaryl optionally fused with a benzene ring; X: a bond, lower alkylene or lower alkenylene optionally substituted by hydroxy or lower alkyl, carbonyl, or a group represented by —NH—(when X is lower alkylene optionally substituted by lower alkyl which may be bonded to the hydrogen atom bonded to a constituent carbon atom of ring B to form lower alkylene to thereby form a ring); A: a lower alkylene or a group represented by -(lower alkylene)—O—; $R^{1a}$ and $R^{1b}$: the same or different and each hydrogen or lower alkyl; $R^2$: hydrogen or halogeno; and Z: nitrogen or a group represented by =CH—. The compounds are useful as a diabetes remedy which not only functions to both accelerate the secretion of insulin and enhance insulin sensitivity but has an antiobestic action and an antihyperlipemic action based on its selective stimulative action on a $\beta_3$ receptor.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2, 7 and 8 are cancelled.

Claims 1, 3-5 and 11 are determined to be patentable as amended.

Claims 9, 10, 13 and 14, dependent on an amended claim, are determined to be patentable.

New claims 15-17 are added and determined to be patentable.

Claims 6 and 12 were not reexamined.

1. A compound of formula (I):

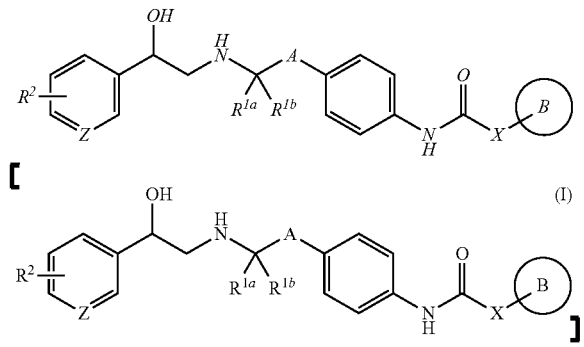

in the formula, each of the symbols means as follows:
   ring B is a *nitrogen-containing* heteroaryl group which is unsubstituted substituted and is optionally fused with a benzene ring;
   X is [a bond, or] a lower alkylene or an alkenylene, both of which are unsubstituted or substituted with hydroxy or a lower alkyl group, or X is a carbonyl or a group represented by —NH—, and when X is a lower alkylene which is substituted with a lower alkyl group, a carbon atom of the ring B optionally bonds with the lower alkyl group so that a ring is formed;
   A is [a lower alkylene] *methylene, ethylene,* or a group represented by [-lower alkylene-O—] —*CH$_2$O*—;
   $R^{1a}$, $R^{1b}$ are the same or different and each is a hydrogen atom or a lower alkyl group;
   $R^2$ is a hydrogen atom or a halogen atom; and
   Z is a group represented by =CH—; or a salt thereof.

3. The compound of formula (I) or the salt thereof according to [claim 2] *claim 1*, wherein the ring B is [a heteroaryl group which is] substituted with a substituent chosen from a halogen atom, lower alkyl, lower alkenyl, lower alkynyl, hydroxy, sulfanyl, halogeno lower alkyl, lower alkyl-O—, lower alkyl-S—, lower alkyl-O—CO—, carboxy, sulfonyl, sulfinyl, lower alkyl-SO—, lower alkyl-SO$_2$—, lower alkyl-CO—, lower alkyl-CO—O—, carbamoyl, lower alkyl-NH—CO—, di-lower alkyl-N—CO—, nitro, cyano, amino, lower alkyl-NH—, *and* di-lower alkyl-N—[, aryl-lower alkyl, halogeno aryl-lower alkyl, guanidino, lower alkyl-CO—NH, and lower alkyl-SO$_2$—NH—].

4. The compound of formula (I) or the salt thereof according to claim 3, wherein $R^2$, $R^{1a}$ and $R^{1b}$ are each a hydrogen atom, [and Z is =CH—] *A is methylene, and*

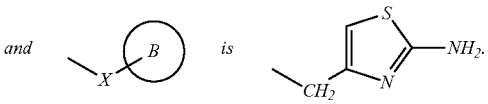

5. A compound of formula (Ia):

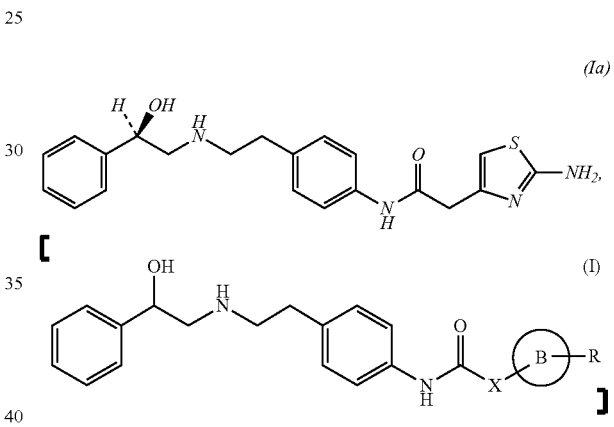

[in the formula, each of the symbols means as follows:
   ring B is a heteroaryl group;
   X is a bond or a lower alkylene group;
   R is a hydrogen atom, a halogen atom, a lower alkyl group, amino group, an aryl lower alkyl group, or a halogeno aryl-lower alkyl group;] or a salt thereof.

11. A composition comprising [at least one] *the* compound of formula [(I)] *(Ia)* or the salt thereof as claimed in claim 5, in a pharmaceutically acceptable carrier.

*15. The compound according to claim 4 or the salt thereof, which is an optical isomer.*

*16. A composition comprising at least one compound of formula (I) or the salt thereof as claimed in one of claims 1, 3, 4, and 15 in a pharmaceutically acceptable carrier.*

*17. The composition as claimed in claim 16, wherein the at least one compound of formula (I) or the salt thereof is present in an amount effective for treating diabetes mellitus in a human or animal patient in need of such treating.*

\* \* \* \* \*